US011078262B2

(12) United States Patent
Hughes et al.

(10) Patent No.: US 11,078,262 B2
(45) Date of Patent: Aug. 3, 2021

(54) HIGH VISCOSITY MACROMOLECULAR COMPOSITIONS FOR TREATING OCULAR CONDITIONS

(75) Inventors: Patrick M. Hughes, Aliso Viejo, CA (US); Gerald W. DeVries, Laguna Hills, CA (US); Robert T. Lyons, Laguna Hills, CA (US); John T. Trogden, Anaheim, CA (US); Scott M. Whitcup, Laguna Hills, CA (US)

(73) Assignee: ALLERGAN, INC., Irvine, CA (US)

( * ) Notice: Subject to any disclaimer, the term of this patent is extended or adjusted under 35 U.S.C. 154(b) by 37 days.

(21) Appl. No.: 11/742,350

(22) Filed: Apr. 30, 2007

(65) Prior Publication Data
US 2008/0268051 A1 Oct. 30, 2008

(51) Int. Cl.
*C07K 16/22* (2006.01)
*A61K 47/34* (2017.01)
*A61K 38/39* (2006.01)
*A61K 9/00* (2006.01)
*C12N 15/113* (2010.01)
*A61K 9/08* (2006.01)
*A61K 39/00* (2006.01)

(52) U.S. Cl.
CPC ............ *C07K 16/22* (2013.01); *A61K 9/0048* (2013.01); *A61K 9/08* (2013.01); *A61K 38/39* (2013.01); *A61K 47/34* (2013.01); *C12N 15/1138* (2013.01); *A61K 2039/505* (2013.01); *C07K 2317/24* (2013.01); *C12N 2310/14* (2013.01); *C12N 2310/315* (2013.01); *C12N 2310/317* (2013.01); *C12N 2310/332* (2013.01); *C12N 2320/32* (2013.01)

(58) Field of Classification Search
CPC .. A61K 9/0048; A61K 9/08; A61K 2039/505; A61K 39/395; A61K 47/643; C07K 16/22
See application file for complete search history.

(56) References Cited

U.S. PATENT DOCUMENTS

| 166,331 | A | 8/1875 | Bean |
| 5,166,331 | A | 11/1992 | Della et al. |
| 5,844,099 | A | 12/1998 | Stahl et al. |
| 6,329,386 | B1 | 12/2001 | Mollison |
| 6,376,517 | B1 | 4/2002 | Ross et al. |
| 6,378,526 | B1* | 4/2002 | Bowman et al. ............. 128/898 |
| 6,469,158 | B1 | 10/2002 | Usman et al. |
| 6,506,559 | B1 | 1/2003 | Fire et al. |
| 6,818,418 | B1 | 11/2004 | Lipovsek et al. |
| 6,818,447 | B1 | 11/2004 | Pavco et al. |
| 6,951,725 | B2 | 10/2005 | Kurz et al. |
| 2002/0123505 | A1 | 9/2002 | Mollison et al. |
| 2004/0259155 | A1 | 12/2004 | Chan et al. |
| 2005/0064010 | A1 | 3/2005 | Cooper et al. |
| 2005/0074865 | A1 | 4/2005 | Afeyan et al. |
| 2005/0101582 | A1* | 5/2005 | Lyons .................. A61K 31/573 514/179 |
| 2005/0233344 | A1 | 10/2005 | McSwiggen et al. |
| 2005/0250737 | A1 | 11/2005 | Hughes et al. |
| 2006/0141049 | A1* | 6/2006 | Lyons et al. .................. 424/489 |
| 2006/0148705 | A1* | 7/2006 | Daly ...................... C07K 14/71 514/8.1 |
| 2006/0182783 | A1 | 8/2006 | Hughes et al. |
| 2006/0258698 | A1 | 11/2006 | Mudumba et al. |
| 2007/0203089 | A1* | 8/2007 | Rodrigues et al. ............. 514/44 |
| 2008/0241252 | A1 | 10/2008 | Lyons et al. |

FOREIGN PATENT DOCUMENTS

| EP | 0 244 178 | 11/1987 |
| EP | 244 178 A2 | 11/1987 |
| EP | 244178 A2 * | 11/1987 |
| WO | WO 92/02258 | 2/1992 |
| WO | WO 93/13121 | 7/1993 |
| WO | WO 94/02501 | 2/1994 |
| WO | WO 94/19023 | 9/1994 |
| WO | WO 01/75164 | 10/2001 |
| WO | WO 02/096927 | 12/2002 |
| WO | WO 03/070910 | 8/2003 |
| WO | WO 03/070918 | 8/2003 |
| WO | WO 03/074654 | 9/2003 |
| WO | WO 05/019453 | 3/2005 |
| WO | WO 05/028649 | 3/2005 |
| WO | WO 05/044981 | 5/2005 |
| WO | WO 2005/046641 | 5/2005 |
| WO | WO2005/072701 | 8/2005 |
| WO | WO 2005/078097 | 8/2005 |
| WO | WO2006/086750 | 8/2006 |
| WO | WO2007/037849 | 4/2007 |
| WO | WO2007/047607 | 4/2007 |
| WO | WO07/084765 A | 7/2007 |
| WO | WO2008/070402 | 6/2008 |
| WO | WO2008/121665 | 10/2008 |

OTHER PUBLICATIONS

Ng et al., Targeting angiogenesis, the underlying disorder in neovascular age-related macular degeneration, Can. J. Ophthalmol. 40(3):352-68, 2005.*
Pieramici et al. Bevacizumab in the treatment of ocular disease. Retina Today, pp. 30-33, Mar. 2006.*
Lowry et al. Thermal stability of sodium hyaluronate in aqueous solution. Journal of Biomedical Materials research. 28:1239-1244, 1994.*

(Continued)

*Primary Examiner* — Vanessa L. Ford
*Assistant Examiner* — Sandra E Dillahunt
(74) *Attorney, Agent, or Firm* — Nathan S. Smith; Christopher J. Betti; Morgan, Lewis & Bockius LLP

(57) ABSTRACT

Anti-angiogenesis compositions, and methods of using such compositions, useful for injection into the vitreous of human eyes are provided. Such compositions include MAAC solutions or particles present in a therapeutically effective amount, a viscosity-inducing component, and an aqueous carrier component. The compositions have viscosities at about 25° C. of at least about 10 cps or about 100 cps at a shear rate of 0.1/second. In a preferred embodiment, the viscosity at 25° C. is in the range of from about 80,000 cps to about 300,000 cps.

14 Claims, 1 Drawing Sheet
Specification includes a Sequence Listing.

(56) References Cited

OTHER PUBLICATIONS

Zhu et al. Inhibition of tumor growth and metastasis by targeting tumor associated angiogenesis with antagonists to the receptors of vascular endothelial growth factor. Investigational New Drugs 17: 195-212, 1999.*
Al-Aswad. Anti-VEGF drugs and neovascular glaucoma. Review of Ophthalmology, 2007; 14(3):84-86.*
Ran et al. Evaluation of Novel Antimouse VEGFR2 Antibodies as Potential Antiangiogenic or Vascular Targeting Agents for Tumor Therapy. Neoplasia, 2003; 5(4):297-307.*
Vajdos et al. Comprehensive Functional Maps of the Antigen binding Site of an Anti-ErbB2 Antibody Obtained with Shotgun Scanning Mutagenesis. Journal of Molecular Biology. Jul. 5, 2002;320(2):415-28.*
Brown et al. Tolerance to Single, but Not Multiple, Amino Acid Replacements in Antibody VH, CDR2. Journal of Immunology. May 1996;156(9):3285-91.*
Bowie et al. Deciphering the Message in Protein Sequences: Tolerance to Amino Acid Substitutions. Science, 1990, 247:1306-1310.*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. Journal of Cell Biology. 111:2129-2138, 1990.*
Lazar et al. Transforming Growth Factor ox: Mutation of Aspartic Acid 47 and Leucine 48 Results in Different Biological Activities. Molecular and Cellular Biology, 8:1247-1252, 1988.*
Bork. Powers and Pitfalls in Sequence Analysis: The 70% Hurdle. Genome Research, 2000,10: 398-400.*
Olsen et al. Pharmokinetics of pars plana intravitreal injections versus microcannula suprachoroidal injections of bevacizumab in a porcine model. Investigative Ophthalmology and Visual Science, 2011; 52(7):4749-4756.*
Yu et al. A Humanized Anti-VEGF Rabbit Monoclonal Antibody Inhibits Angiogenesis and Blocks Tumor Growth in Xenograft Models. PLOS One 5(2): E9072.*
Zhu et al. Inhibition of tumor growth and metastasis by targeting tumor associated angiogenesis with antagonists to the receptors of vascular endothelial growth factor. Investigational New Drugs 17: 195-212, 1999 (Year: 1999).*
Vajdos et al. Comprehensive Functional Maps of the Antigen binding Site of an Anti-ErbB2 Antibody Obtained with Shotgun Scanning Mutagenesis. Journal of Molecular Biology. Jul. 5, 2002;320(2):415-28 (Year: 2002).*
Brown et al. Tolerance to Single, but Not Multiple, Amino Acid Replacements in Antibody VH, CDR2. Journal of Immunology. MAy 1996;156(9):3285-91 (Year: 1996).*
Bowie et al. Deciphering the Message in Protein Sequences: Tolerance to Amino Acid Substitutions. Science, 1990, 247:1306-1310 (Year: 1990).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. Journal of Cell Biology. 111:2129-2138, 1990 (Year: 1990).*
Lazar et al. Transforming Growth Factor ox: Mutation of Aspartic Acid 47 and Leucine 48 Results in Different Biological Activities. Molecular and Cellular Biology, 8:1247-1252, 1988 (Year: 1988).*
Bork. Powers and Pitfalls in Sequence Analysis: The 70% Hurdle. Genome Research, 2000,10: 398-400 (Year: 2000).*
Yu et al. A Humanized Anti-VEGF Rabbit Monoclonal Antibody Inhibits Angiogenesis and Blocks Tumor Growth in Xenograft Models. PLOS One 5(2): E9072 (Year: 2010).*
U.S. Appl. No. 11/370,301, Aug. 17, 2006, Hughes et al., filed Mar. 8, 2006.
U.S. Appl. No. 11/364,687, Mar. 15, 2007, Hughes et al., filed Feb. 27, 2006.
U.S. Appl. No. 60/721,600, Hughes et al., filed Sep. 28, 2005.
U.S. Appl. No. 11/116,698, Dec. 22, 2005, Hughes et al., filed Apr. 27, 2005.
U.S. Appl. No. 60/567,423, Hughes et al., filed Apr. 30, 2004.
U.S. Appl. No. 11/695,527, Lyons et al., Apr. 2, 2007.
U.S. Appl. No. 11/091,977, Nov. 10, 2005, Hughes et al., filed Mar. 28, 2005.
U.S. Appl. No. 11/354,415, Jun. 29, 2006, Lyons et al., filed Feb. 14, 2006.
U.S. Appl. No. 60/519,237, Lyons et al., filed Nov. 12, 2003.
U.S. Appl. No. 60/530,062, Lyons et al., filed Dec. 16, 2003.
Adams et al., *The Biochemistry of the Nucleic Acids* (11$^{th}$ ed 1992).
Aiello L.P., et al., Vascular endothelial growth factor in ocular fluid of patients with diabetic retinopathy and other retinal disorders, New Engl. J. Med. 331: 1480-1487 (1994).
Antcliff R., et al Marshall J., *The Pathogenesis of Edema in Diabetic Maculopathy*, Semin Ophthalmol 1999; 14:223-232.
Connolly D.T., et al., Tumor vascular permeability factor stimulates endothelial cell growth and angiogenesis. J. Clin. Invest. 84: 1470-1478 (1989).
Einmahl S. et al, *Evaluation of a Novel Biomaterial in the Suprachoroidal Space of the Rabbit Eye*, Invest Ophthal & Vis Sci 43(5); 1533-1539 (2002).
Einmahl S. et al, *Therapeutic Applications of Viscous and Injectable Poly(Ortho Esters)*, Adv Drug Del Rev 53 (2001) 45-73.
Goodman and Ro, Peptidomimetics for Drug Design, in "Burger's Medicinal Chemistry and Drug Discovery" vol. 1 (ed. M.E. Wolff; John Wiley & Sons 1995), pp. 803-861).
Huh et al., Oncogene 24:790-800 (Jan. 27, 2005).
Kim et al., Am. J. Pathology 165:2177-2185 (2004).
Mamluk et al., J. Clin. Oncol. 23:3150 (supp. Jun. 1, 2005).
Mustonen T. et al., Endothelial receptor tyrosine kinases involved in angiogenesis, J. Cell Biol. 129: 895-898 (1995).
Pe'er J. et al., *Vascular Endothelial Growth Factor Upregulation in Human Central Retinal Vein Occlusion*, Ophthalmology 1998; 105:412-416.
Sambrook & Russell, Molecular Cloning: A Laboratory Manual (3d ed. Cold Spring Harbor Laboratory Press 2001).
Tkaei et al., Cancer Res. 64:3365-3370 (May 15, 2004).
U.S. Appl. No. 11/695,527, filed Apr. 2, 2007.
European Search Report—Application No. 12199057.6-1456— dated May 28, 2013, 11 pages.

* cited by examiner

Variable Heavy

```
A.4.6.1.  EIQLVQSGPELKQPGETVRISCKASGYTETNYGMNWVKQAPGKGLKWMG
                *   ** *  *** * *         *   * *
F(ab)-12  EVQLVESGGGLVQPGGSLRLSCAASGYTFTNYGMNWVRQAPGKGLEWVG
                      * **** *          *
humIII         EVQLVESGGGLVQPGGSLRLSCAASGFTFSSYAMSWVKQAPGKGLEWVS
               1    10    20    30    40
```

```
A.4.6.1.  WINTYTGEPTYAADFKRRFTFSLETSASTAYLQISNLKNDDTATYFCAK
                      * *       *** *** * *
F(ab)-12  WINTYTGEPTYAADFKRRFTFSLDTSKSTAYLQMNSLRAEDTAVYYCAK
          * **** *** *** * ***** *          *
humIII         VISGDGGSTYYADSVKGRFTISRDNSKNTLYLQMNSLRAEDTAVYYCAR
               50 a    60    70    80 abc    90
```

```
A.4.6.1  YPHYYGSSHWYFDVWGAGITVTVSS
                          * *
F(ab)-12 YPHYYGSSHWYFDVWGQGTLVTVSS
              *        *
humIII         G----------FDYWGQGTLVTVSS
                  110
```

Variable Light

```
A.4.6.1  DIQMTQTTSSLSASLGDRVIISCSASQDISNYLNWYQQKPDGTVKVLIY
              **    *  * *          ****
F(ab)-12 DIQMTQSPSSLSASVGDRVTITCSASQDISNYLNWYQQKPGCAPKVLIY
              *  **  *         *
humKI          DIQMTQSPSSLSASVGDRVTITCRASQSISNYLAWYQQKPGCAPKLLTY
               1    10    20    30    40
```

```
A.4.6.1  FTSSLHSGVPSRFSGSGSGTDYSLTISNLEPEDIATYYCQQYSTVPWTF
                               ** * * *
F(ab)-12 FTSSLHSGVPSRFSGSGSGTDFTLTISSLQPEDFATYYCQQYSTYPWTF
         **  *                              ***
humKI          AASSLESGVPSRFSGSGSGTDFTLTISSLQPEDFATYYCQQYNSLPWTF
               50    60    70    80    90
```

```
A.4.6.1  GGGTKLEIKR
            * *
F(ab)-12 GQGTKVEIKR humKI          GQGTKVBIKR
               100
```

Fig. 1. Amino acid sequence of variable heavy and light domains of: muMAb VEGF A.4.6.1 (SEQ ID NO: 16 and 19, respectively), humanized F(ab) with optimal VEGF binding [F(ab)-12](SEQ ID NO: 17 and SEQ ID NO: 20, respectively) and human consensus frameworks (*humIII*, heavy subgroup III; *humkI*, light k subgroup I)(SEQ ID NO: 18 and SEQ ID NO: 21). *Asterisks*, differences beween humanized F(ab)-12 and the murine MAb or between F(ab)-12 and the human framework. CDRs are *underlined*.

HIGH VISCOSITY MACROMOLECULAR COMPOSITIONS FOR TREATING OCULAR CONDITIONS

BACKGROUND

The present invention relates to ophthalmically useful compositions comprising a viscosity inducing component and an active pharmaceutical agent. In preferred embodiments, the pharmaceutically active agent can comprise a macromolecular anti-angiogenesis component. The invention also relates to methods for treating and/or preventing ocular conditions, such as anterior ocular conditions and posterior ocular conditions. In a preferred embodiment the present invention relates to extended release and sustained release therapeutic compositions comprising ophthalmically acceptable gels, suspensions, emulsions and other liquid formulations comprising a viscosity inducing component and a macromolecular anti-angiogenesis component.

A pharmaceutical composition (synonymously a "composition") is a formulation which contains at least one active ingredient (for example a macromolecular anti-angiogenesis ["MAA"] component ["MAAC"]), together with a viscosity enhancing component. In certain embodiments the composition may also contain one or more excipients, buffers, carriers, stabilizers, preservatives and/or bulking agents, and is suitable for administration to a patient to achieve a desired effect or result. The pharmaceutical compositions disclosed herein can have diagnostic, therapeutic, cosmetic and/or research utility in various species, such as for example in human patients or subjects.

A variety of ocular conditions involve a disease, ailment or condition which affects or involves the eye or one of the parts or regions of the eye and is characterized to a major or minor degree by angiogenesis (the formation of new blood vessels).

Broadly speaking, the eye includes the eyeball and the tissues and fluids which constitute the eyeball, the periocular muscles (such as the oblique and rectus muscles) and the portion of the optic nerve which is within or adjacent to the eyeball. An anterior ocular condition is a disease, ailment or condition which affects or which involves an anterior (i.e. front of the eye) ocular region or site, such as a periocular muscle, an eyelid or an eyeball tissue or fluid which is located anterior to the posterior wall of the lens capsule or ciliary muscles. Thus, an anterior ocular condition primarily affects or involves, the conjunctiva, the cornea, the conjunctiva, the anterior chamber, the iris, the posterior chamber (anterior to the retina but in posterior to the posterior wall of the lens capsule), the lens or the lens capsule and blood vessels and nerve which vascularize or innervate an anterior ocular region or site.

A condition of the posterior segment (posterior ocular condition) of the eye is a disease, ailment or condition which significantly affects or involves a tissue or cell type in a posterior ocular region or site (that is, in a position posterior to a plane through the posterior wall of the lens capsule), such as the accordingly located parts of the choroid or sclera, vitreous, vitreous chamber, retina, optic nerve (i.e. the optic disc), and blood vessels and nerves which vascularize or innervate a posterior ocular (or posterior segment) region or site.

Thus, a posterior ocular condition can include a disease, ailment or condition, such as for example, macular degeneration (such as non-exudative age-related macular degeneration and exudative age-related macular degeneration); choroidal neovascularization; acute macular neuroretinopathy; macular edema (such as cystoid macular edema and diabetic macular edema); Behcet's disease, retinal disorders, diabetic retinopathy (including proliferative diabetic retinopathy); retinal arterial occlusive disease; central retinal vein occlusion; uveitis (including intermediate and anterior uveitis); retinal detachment; ocular trauma which affects a posterior ocular site or location; a posterior ocular condition caused by or influenced by an ocular laser treatment; posterior ocular conditions caused by or influenced by a photodynamic therapy; photocoagulation; radiation retinopathy; epiretinal membrane disorders; branch retinal vein occlusion; anterior ischemic optic neuropathy; non-retinopathy diabetic retinal dysfunction, retinitis pigmentosa and glaucoma. Glaucoma can be considered a posterior ocular condition because a therapeutic goal can be to prevent the loss of or reduce the occurrence of loss of vision due to damage to or loss of retinal cells or optic nerve cells (i.e. neuroprotection). The infiltrative growth of new blood vessels can disrupt or destroy nervous tissue; thus the inhibition of angiogenesis can also be considered to provide protection to affected neurons.

Macular edema is a major cause of visual loss in patients, and can accompany a number of pathological conditions, including, without limitation, diabetes, central retinal vein occlusion (CRVO) and branch retinal vein occlusion (BRVO). Although laser photocoagulation can reduce further vision loss in patients with diabetic macular edema (DME), vision that has already been decreased by macular edema through neural cell death usually does not improve appreciably by use of laser photocoagulation. Currently, there is no FDA (U.S. Food and Drug Administration) approved treatment for macular edema associated with CRVO. For macular edema associated with BRVO, grid laser photocoagulation may be an effective treatment for some patients.

Diabetic macular edema is characterized abnormal leakage of macromolecules, such as lipoproteins, from retinal capillaries into the extravascular space followed by an oncotic influx of water into the extravascular space. The leakage may be caused by or exacerbated by the growth of new blood vessels (angiogenesis). Abnormalities in the retinal pigment epithelium (RPE) may also cause or contribute to diabetic macular edema.

These abnormalities can allow increased fluid from the choriocapillaries to enter the retina or they may decrease the normal efflux of fluid from the retina to the choriocapillaries. The breakdown of the blood-retina barrier at the level of the retinal capillaries and the retinal pigment epithelium may also be accompanied or caused by changes to tight junction proteins. Antcliff R., et al Marshall J., *The Pathogenesis Of Edema In Diabetic Maculopathy*, Semin Opthalmol 1999; 14:223-232.

Macular edema from venous occlusive disease can result from thrombus formation at the lamina cribrosa or at an arteriovenous crossing. These changes can result in an increase in retinal capillary permeability and accompanying retinal edema. The increase in retinal capillary permeability and subsequent retinal edema can ensue from of a breakdown of the blood retina barrier mediated in part by vascular endothelial growth factor (VEGF), a 45 kD glycoprotein. It is known that VEGF can increase vascular permeability; possibly by increasing phosphorylation of tight junction proteins such as occludin and zonula occluden. Similarly, in human non-ocular disease states such as ascites, VEGF has been characterized as a potent vascular permeability factor (VPF).

Biochemically, VEGF is known to be a major contributor to the increase in the number of capillaries in tissue undergoing angiogenesis. Bovine capillary endothelial cells will proliferate and show signs of tube structures in vitro upon stimulation by VEGF. Upregulation of VEGF is a major component of the physiological response to exercise and its role in angiogenesis is suspected to be a possible treatment in vascular injuries.

VEGF causes an intracellular signaling cascade in endothelial cells. VEGF binding to VEGF receptor-2 (VEGFR-2) initiates a tyrosine kinase signaling cascade that stimulates the production of factors that variously stimulate vessel permeability (epithelial nitric oxide synthase; (eNOS), proliferation/survival (bFGF; basic fibroblast growth factor), migration (intercellular adhesion molecules (ICAMs); vascular cell adhesion molecules (VCAMs); matrix metalloproteases (MMPs)) and finally differentiation into mature blood vessels. As part of the angiogenic signaling cascade, NO (nitric oxide) is widely considered to be a major contributor to the angiogenic response because inhibition of NO significantly reduces the effects of angiogenic growth factors.

The normal human retina contains little or no VEGF; however, hypoxia causes upregulation of VEGF production. Disease states characterized by hypoxia-induced VEGF upregulation include, without limitation, CRVO and BRVO. This hypoxia induced upregulation of VEGF can be inhibited pharmacologically. Pe'er J. et al., *Vascular Endothelial Growth Factor Upregulation In Human Central Retinal Vein Occlusion*, OPHTHALMOLOGY 1998; 105:412-416. It has been demonstrated that anti-VEGF antibodies can inhibit VEGF driven capillary endothelial cell proliferation. Thus, attenuation of the effects of VEGF introduces a rationale for treatment of macular edema from venous occlusive disease.

Additionally, overexpression of VEGF causes increased permeability in blood vessels in addition to stimulating angiogenesis. In "wet" or exudative macular degeneration, VEGF causes proliferation of capillaries into the retina. Since the increase in angiogenesis also causes edema, blood and other retinal fluids leak into the retina causing loss of vision. A novel treatment for macular degeneration is to use a MAAC, such as a VEGF inhibiting aptamer, or other VEGF-inhibiting compound, such as a to stop the main signaling cascade for angiogenesis, thereby preventing these symptoms.

European patent application 244 178 A2 (Keller) discloses intravitreal injection of an aqueous solution of dexamethasone, a steroid, and a hyaluronic acid (HA). Einmahl S. et al, *Evaluation Of A Novel Biomaterial In The Suprachoroidal Space Of The Rabbit Eye*, INVEST OPHTHAL & VIS SCI 43 (5); 1533-1539 (2002) discusses injection of a poly (ortho ester) into the suprachoroidal space, and Einmahl S. et al, *Therapeutic Applications Of Viscous And Injectable Poly(Ortho Esters)*, ADV DRUG DEL REV 53 (2001) 45-73, discloses that a poly ortho ester polymer containing fluorouracil markedly degrades five days after intravitreal administration. European Patent Publication EP 0 244 178 describes HA compositions for intraocular injection containing antibiotics or anti-inflammatory agents. Della Valle et al., U.S. Pat. No. 5,166,331 discusses purification of different fractions of HA for use as a substitute for intraocular fluids and as a topical ophthalmic drug carrier.

Formulations of macromolecules for intraocular use are known, See e.g. application Ser. No. 11/370,301; 11/364,687; 60/721,600; 11/116,698 and 60/567,423. Additionally, formulations of a tyrosine kinase inhibitor in a high viscosity gel for ocular use is known. See e.g. U.S. patent application Ser. No. 11/695,527. Furthermore, use of the steroid triamcinolone in a high viscosity gel for ocular use is known. See e.g. U.S. patent application Ser. Nos. 10/966,764; 11/091,977; 11/354,415; 60/519,237, and; 60/530,062. With regard to use of a tyrosine kinase inhibitor in a high viscosoity gel see U.S. application Ser. No. 11/695,527.

SUMMARY

In one embodiment the present invention provides formulations comprising one or more MAAC in a biocompatible viscous carrier suitable for intraocular (including, without limitation, intravitreal, subconjuntival, and subretinal) injection or placement for treating ocular angiogenesis, particularly angiogenesis in the retina, including the macula; the choroid, the sclera and other features of the posterior segment of the eye, as may be manifested in the development of, e.g., macular edema, dry and wet macular degeneration, particularly exudative macular degeneration, diabetic retinopathy and other disorders and diseases involving angiogenesis. In a preferred embodiment, the carrier comprises a hyaluronic acid component, preferably at least one polyhyaluronic acid component of defined average molecular weight.

Definitions

As used herein, the words or terms set forth below have the following definitions.

"About" means that the item, parameter or term so qualified encompasses a range of plus or minus ten percent above and below the value of the stated item, parameter or term.

"Administration", or "to administer" means the step of giving (i.e. providing) a pharmaceutical composition to a subject. The pharmaceutical compositions disclosed herein can be "locally administered", that is administered at or in the vicinity of the site at which a therapeutic result or outcome is desired. For example to treat an ocular condition (such as for example a macular edema, or macular degeneration) intravitreal injection or implantation of a therapeutic composition such as active agent-containing viscous composition can be carried out, and is an example of local administration.

"Entirely free (i.e. "consisting of" terminology) means that within the detection range of the instrument or process being used or referenced, the substance cannot be detected or its presence cannot be conclusively confirmed.

"Essentially free" means that only trace amounts of other substances, or a reference substance (such trace amounts not having a substantial effect in the application), can be detected.

By a "macromolecular" therapeutic agent or anti-angiogenesis component is meant that a therapeutic agent consists of, consists essentially of, or comprises a peptide or oligonucleotide as such terms are defined herein.

By an "ocular condition" is meant a disease, ailment or condition which affects or involves the eye or one of the parts or regions of the eye. Broadly speaking, the eye includes the eyeball and the tissues and fluids which constitute the eyeball, the periocular muscles (such as the oblique and rectus muscles) and the portion of the optic nerve which is within or adjacent to the eyeball.

An "anterior ocular condition" is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber (behind the iris but in front of the posterior wall of the lens capsule), the lens or the lens capsule and blood vessels and nerve which vascularize or innervate an anterior ocular region or site.

Thus, an anterior ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

A "posterior ocular condition" is a disease, ailment or condition which primarily affects or involves a posterior ocular region or site such as choroid or sclera (in a position posterior to a plane through the posterior wall of the lens capsule), vitreous, vitreous chamber, retina, retinal pigmented epithelium, Bruch's membrane, optic nerve (i.e. the optic disc), and blood vessels and nerves which vascularize or innervate a posterior ocular region or site.

Thus, a posterior ocular condition can include a disease, ailment or condition, such as for example, acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

"Pharmaceutical composition" means a formulation in which an active ingredient (the active agent) can be an inhibitor of angiogenesis, such as a MAAC. The word "formulation" means that there is at least one additional ingredient in the pharmaceutical composition besides the active ingredient. A pharmaceutical composition is therefore a formulation which is suitable for diagnostic or therapeutic administration (e.g., by intraocular injection or by insertion of a depot or implant) to a subject, such as a human patient.

The term "peptide", "polypeptide", and protein includes naturally occurring and non-naturally occurring L-amino acids, R-amino acids, and peptidomimetics. A peptidomimetic comprises a peptide-like molecule that is able to serve as a model for a peptide substrate upon which it is structurally based. Such peptidomimetics include chemically modified peptides, peptide-like molecules containing non-naturally occurring amino acids, and peptoids, which are peptide-like molecules resulting from oligomeric assembly of N-substituted glycines (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861), hereby incorporated by reference herein.

A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; an α,α-dialkyl-glycine or α-aminocycloalkane carboxylic acid; an Nα-Cα cyclized amino acid; an Nα-methylated amino acid; a β- or γ-amino cycloalkane carboxylic acid; an α,β-unsaturated amino acid; a β,β-dimethyl or β-methyl amino acid; a β-substituted-2,3-methano amino acid; an NCδ or Cα-Cδ cyclized amino acid; or a substituted proline or another amino acid mimetic. In addition, a peptidomimetic which mimics peptide secondary structure can contain, for example, a nonpeptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylenesulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein. The term "polypeptide" shall include peptidomimetics unless expressly indicated otherwise.

"Substantially free" means present at a level of less than one percent by weight of the pharmaceutical composition.

The term "treat", "treating", or "treatment" as used herein, refers to reduction or resolution or prevention of an ocular condition, ocular injury or damage, or to promote healing of injured or damaged ocular tissue.

The term "therapeutically effective amount" as used herein, refers to the level or amount of agent needed to treat an ocular condition, or reduce or prevent ocular injury or damage without causing significant negative or adverse side effects to the eye or a region of the eye.

An "oligonucleotide" or "nucleic acid" according to the present invention may comprise two or more naturally occurring or non-naturally occurring deoxyribonucleotides or ribonucleotides linked by a phosphodiester linkage, or by a linkage that mimics a phosphodiester linkage to a therapeutically useful degree. According to the present invention, an oligonucleotide will normally be considered to be single-stranded unless otherwise obvious from the context, and a nucleic acid may be single stranded or double stranded. Additionally, an oligonucleotide or nucleic acid may contain one or more modified nucleotide; such modification may be made in order to improve the nuclease resistance of the oligonucleotide, to improve the hybridization ability (i.e., raise the melting temperature or Tm) of the resulting oligonucleotide, to aid in the targeting or immobilization of the oligonucleotide or nucleic acid, or for some other purpose.

Such modifications may include oligonucleotide derivatives having modifications at the nitrogenous base, including replacement of the amino group at the 6 position of adenosine by hydrogen to yield purine; substitution of the 6-keto oxygen of guanosine with hydrogen to yield 2-amino purine, or with sulphur to yield 6-thioguanosine, and replacement of the 4-keto oxygen of thymidine with either sulphur or hydrogen to yield, respectively, 4-thiothymidine or 4-hydrothymidine. All these nucleotide analogues can be used as reactants for the synthesis of oligonucleotides. Other substituted bases are known in the art. See, e.g., Cook et al., International Publication No. WO 92/02258, entitled "*Nuclease Resistant, Pyrimidine Modified Oligonucleotides that Detect and Modulate Gene Expression,*" which is incorporated by reference herein. Base-modified nucleotide derivatives can be commercially obtained for oligonucleotide synthesis.

Similarly, a number of nucleotide derivatives have been reported having modifications of the ribofuranosyl or deoxyribofuranosyl moiety. See, e.g., Cook et al., International Publication No. WO 94/19023, entitled "Cyclobutyl Antisense Oligonucleotides, Methods of Making and Use Thereof"; McGee et al., International Publication No. WO 94/02501, entitled "Novel 2'-O-Alkyl Nucleosides and Phosphoramidites Processes for the Preparation and Uses Thereof"; and Cook, International Publication No. WO 93/13121, entitled "Gapped 2'-Modified Oligonucleotides." Each of these publications is hereby incorporated by reference herein.

Most oligonucleotides comprising such modified bases have been formulated with increased cellular uptake, nuclease resistance, and/or increased substrate binding in mind. In other words, such oligonucleotides are described as therapeutic gene-modulating agents.

Nucleic acids having modified nucleotide residues exist in nature. Thus, depending on the type or source, modified bases in RNA can include methylated or dimethylated bases, deaminated bases, carboxylated bases, thiolated bases and bases having various combinations of these modifications. Additionally, 2'-O-alkylated bases are known to be present in naturally occurring nucleic acids. See e.g., Adams et al., *The Biochemistry of the Nucleic Acids* (11$^{th}$ ed 1992), hereby incorporated by reference herein.

Viscosity values in the specification or the claims are mean the viscosity at 25° C., unless specifically indicated otherwise.

Each range of values (amounts, viscosities, temperatures and the like) specifically includes, and shall be regarded as containing a complete written description of) all values and sub-ranges between the minimum and maximum.

The present compositions are highly suitable for intravitreal administration into the posterior segments of eyes without requiring any washing step, while providing for reduced ocular, for example, retinal, damage when used in an eye. Overall, the present compositions are easily and effectively injectable into the posterior segment of an eye of a human or animal. An advantage of the formulations of the present invention is that the MAAC is present in a viscous carrier comprising a viscosity inducing component which is biologically compatible, that is, has no substantial deleterious or cytotoxic effects on the cells of the eye.

In one broad aspect of the present invention, compositions useful for injection into a posterior segment of an eye of a human or animal are provided. Such compositions comprise a MAAC, a viscosity inducing component, and an aqueous carrier component. The MAAC is present in a therapeutically effective amount. The MAAC is preferably present in the compositions in solution, but may initially be present in somewhat or partly insoluble form, such as in a plurality of particles.

The present compositions may include a MAAC in an amount of up to about 25% (w/v) or more of the composition. In one very useful embodiment, the MAAC is present in an amount up to at least about 80 mg/ml of composition. Preferably, the MAAC is present in an amount in a range of about 1% to about 10% or about 20% (w/v) of the composition, or about 0.05 mg per 100 µl, or about 0.1 mg per 100 µl, or about 0.2 mg per 100 µl, or about 0.4 mg per 100 µl, or about 0.5 mg per 100 µl, or about 1.0 mg per 100 µl or about 2.0 mg per 100 µl, or about 4.0 mg per 100 µl, or about 5.0 mg per 100 µl, or about 6.0 mg per 100 µl, or about 7.0 mg per 100 µl, or about 8.0 mg per 100 µl, or about 10 mg per 100 µl, or about 20 mg per 100 µl, or about 40 mg per 100 µl, or about 60 mg per 100 µl, or about 80 mg per 100 µl, or any of the ranges or concentrations between about 0.05 mg per 100 µl and 80 mg pere 100 µl.

In particular, the MAACs of the present invention are inhibitors of angiogenesis, particularly ocular angiogenesis, such as choroidal neovascularization (CNV) accompanying a condition such as macular degeneration, in particular, though not exclusively, exudative macular degeneration, diabetic retinopathy, retinal ischemia and macular edema.

Vascular epithelial growth factor (VEGF-A) is a generic name for a family of signaling proteins involved in angiogenesis (the growth of blood vessels from pre-existing vasculature). VEGF also enhances microvascular permeability. This family of proteins comprises splice variants resulting from alternative splicing of a single gene. There are other VEGF-like proteins, including VEGF-B, VEGF-C and VEGF-D and PlGF.

All members of the VEGF family stimulate cellular responses by binding to tyrosine kinase receptors (the VEGFRs) on the cell surface. Ligand binding induces dimerization which activates the tyrosine kinase activity of the receptor. This leads to receptor autophosphorylation and the initiation of intracellular signal transduction cascades causing the receptors to dimerize and become activated through transphosphorylation involving the tyrosine kinase. The VEGF receptors have an extracellular portion consisting of 7 immunoglobulin-like domains, a single transmembrane spanning region and an intracellular portion containing a split tyrosine kinase domain.

Various approaches have been made to inhibit either VEGF itself or the VEGFR present in the eye in order to prevent angiogenesis. Thus, monoclonal antibodies such as ranibizumab (LUCENTIS®; rhuFab V2) or bevacizumab (AVASTIN®; rhuMab-VEGF); nucleic acids (aptamers such as MACUGEN®, (pegaptanib) a PEGylated RNA aptamer, and siRNAs directed to VEGF RNA), and both protein and small molecule tyrosine kinase inhibitors have been investigated for the treatment of angiogenesis associated with conditions of the posterior segment.

As stated above, hypoxia is known to upregulate VEGF expression, and VEGF expression was shown to be correlated with iris neovascularization in primate models of ischemic retinal vein occlusion and retinal neovascularization. Injection of VEGF in normal primate eyes produces iris neovascularization, neovascular glaucoma, and retinal microaniopathy. Inhibition of VEGF through the use of chimeric proteins acting as soluble VEGF receptors suppresses neovascularization in these models.

Human clinical studies have also confirmed the association of VEGF expression with pathologic ocular neovascularization. Measurements of vitreous VEGF levels demonstrated significantly higher VEGF concentrations in patients with active proliferative diabetic retinopathy compared with patients with other retinal disorders not characterized by abnormal blood vessel growth. Another study that analyzed both aqueous and vitreous levels of VEGF in a variety of conditions characterized by ocular neovascularization correlated elevated VEGF concentrations in ocular fluids of patients with active neovascularization.

Inhibition of angiogenesis (and particularly VEGFR-associated angiogenesis) in the posterior segment of the eye may be accomplished using any of a number of MAACs that have activity against activation of the VEGFR, either directly or through inhibition of VEGF itself.

According to one major embodiment of the present invention, the therapeutic component described herein comprises one or more MAAC.

Macromolecular therapeutic agents according to the present invention include peptides, polypeptides, proteins, oligonucleotides, and nucleic acids. In particularly preferred embodiments of the invention, the therapeutic agent may comprise a protein, a polyclonal or monoclonal antibody, an antibody fragment, such as a monovalent fraction antigen-binding papain fragment (Fab) or a bivalent fraction antigen binding pepsin fragment (F' ab$_2$). Additionally, the antibodies or antibody fragments may be naturally occurring or genetically engineered. For example, the term "antibodies" may include chimeric antibodies comprising human $L_C$ and $H_C$ regions and $L_V$ and $H_V$ regions from another species, for example, from mouse cells. Chimeric antibodies are useful in the design of antibody-based drugs, since the use of unaltered mouse antibodies induces the production of human anti-mouse immunoglobulins and resultant clearance and reduction of efficacy.

However, chimeric antibodies, while having reduced immunogenicity as compared to the rodent antibody, do not solve all the problems that exist in the use of antibodies as drugs. For example, to minimize allotypic variation in the constant regions a human consensus sequence can be used representing the most common allotype in the general population. A further refinement has been used, called complimentarily determining region (CVDR) grafting. In this method, only the three antigen biding sites (formed by the three CDRs of the heavy chain and the three CDRs of the light chain) are excised from the murine antibodies and the nucleic acid regions encoding these CDRs have been inserted (or "grafted") into a nucleic acid coding sequence encoding the framework region of the human antibody.

Further refinements may comprise what has been termed "reshaping", "veneering" and "hyperchimerization". In reshaping, the rodent variable region is compared with the consensus sequence of the protein sequence subgroup to which it belongs, as is the human framework compared with a consensus of the framework sequence for the antibody family to which it belongs. This analysis can identify amino acid residues that may be the result of mutation during the affinity maturation process; these residues are called "idiosyncratic". By incorporating the more common human residues in these positions, immunogenicity problems resulting from the idiosyncratic residues can be minimized.

Humanization by hyperchimerization involves a comparison of the human and murine non-CDR variable region sequences and the one with the highest homology is selected as the acceptor framework. Again, idiosyncratic residues are replaced with more highly conserved human ones. Those non-CDR residues that may interact with the CDR residues are identified and inserted into the framework sequence.

Veneering involves determining the three dimensional conformation of a humanized murine antibody and replacing the expose surface amino acids with those commonly found in human antibodies. In the first step the most homologous human variable regions are selected and compared to the corresponding mouse variable regions. In the second step, the mouse framework residues differing from the human framework are replaced with the human residues; only those residues fully or partially exposed at the surface of the antibody are changed.

While the humanization of antibodies provides therapeutic advantages not available in the use of murine or chimeric antibodies alone, new classes of peptide and nucleic acid agents have been engineered to bind strongly to a desired target thereby antagonizing the normal activity of the target.

For example, fibronectins and fibronectin-related molecules (hereinafter collectively referred to as "fibronectins"), are multi-domain glycoproteins found in a soluble form in plasma, and in an insoluble form in loose connective tissue and basement membranes. They contain multiple copies of 3 repeat regions (types I, II and III), which bind to a variety of substances including heparin, collagen, DNA, actin, fibrin and fibronectin receptors on cell surfaces. Fibronectins are involved in a number of important functions: e.g., wound healing; cell adhesion; blood coagulation; cell differentiation and migration; maintenance of the cellular cytoskeleton; and tumor metastasis. The role of fibronectin in cell differentiation is demonstrated by the marked reduction in the expression of its gene when neoplastic transformation occurs. Cell attachment has been found to be mediated by the binding of the tetrapeptide RGDS to integrins on the cell surface although related sequences can also display cell adhesion activity.

Plasma fibronectin occurs as a dimer of 2 different subunits, linked together by 2 disulphide bonds near the C-terminus. The difference in the 2 chains occurs in the type III repeat region and is caused by alternative splicing of the mRNA from one gene.

The fibronectin type III (FnIII) repeat region is an approximately 100 amino acid domain, different tandem repeats of which contain binding sites for DNA, heparin and the cell surface. The superfamily of sequences believed to contain FnIII repeats represents 45 different families, the majority of which are involved in cell surface binding in some manner, or are receptor protein tyrosine kinases, or cytokine receptors.

Because a common characteristic of fibronectins is that they are involved in intermolecular binding, and due to the common scaffolding structure of the fibronectin molecule, such molecules are very useful templates for making and producing selective binding molecules capable of acting as antibody mimics. Such antibody mimics will often provide interference in preventing the interaction of the target "antigen" molecule or moiety with a binding partner, such as a selective or specific receptor. Thus, such selectively binding fibronectin molecules comprise ideal templates for making, for example, receptor antagonists.

The FnIII loops comprise regions that may be subjected to random mutation and directed evolutionary schemes of iterative rounds of target binding, selection, and further mutation in order to develop useful therapeutic tools. Fibronectin based "addressable" therapeutic binding molecules (hereinafter "FATBIMs") may be useful in the inhibition of certain ophthalmically deleterious ligands or receptors, such as VEGF. FATBIMs include the species of fibronectin-based binding molecules termed ADNECTINS™ by Adnexus (formerly known as Compound Therapeutics, Inc.).

Whether nucleic acid or polypeptide in nature, macromolecular therapeutic components present specific challenges when making intraocular drug delivery systems. The drug formulation must above all be substantially non-toxic to intraocular tissues. When such a formulation comprises a liquid carrier, it is very advantageous for the carrier component to possess a refractive index that is substantially similar to that of the aqueous humor or the vitreous humor (depending upon in which chamber the formulation is introduced), so that the patient's vision is not substantially adversely affected, such as by changes in focus, following administration, for example injection, of the therapeutic composition the intraocular tissues. Formulations having a refractive index of water (approximately 1.33, depending on the wavelength of light), for example, could create enough of a difference in refractive index at the boundary of injected formulation and the vitreous humor following injection to adversely affect vision in the patient during a time following administration.

Additionally, given the complex folding necessary to give proteins their biological activity, it is surprising that a solution comprising relatively high concentrations of a given viscosity enhancing component, such as 2% hyaluronic acid, at an given pH, such as between about 6.5 to about 8.0, would permit macromolecular MAACs, such as proteins or polypeptides, to retain a biologically active conformation without denaturation. As opposed to "small" molecules, which either lack a tertiary structure or are less dependent for their activity on their three dimensional conformation, proteins are capable of being denatured by any of a variety of changes in their environment, including heat, cold, high salt concentrations, the presence of chaotropes (agents that cause molecular structure to be disrupted; in particular, those structures formed by nonbonding forces such as hydrogen bonding, Van der Waals interactions, and the hydrophobic effect).

Similarly, certain nucleic acids, require e the maintenance of a given three dimensional conformation in order to retain their desired MAAC activity. This is particularly true of certain nucleic acid aptamers, which rely on a biological activity, such as a enzymatic or receptor inhibitory activity for their activity. This is also true of enzymatic nucleic acids such as ribozymes. Again, it is surprising that high concentrations of a viscosity enhancing component in a drug formulation would not lead to loss of this activity through unfolding and denaturation of the nucleic acids' tertiary structure.

In certain embodiments the formulation of the present invention may comprise a suspension of particles or crystals comprising the therapeutic component or of biodegradable polymers within which or on the surface of which a population of the therapeutic component is deposited or incorporated. For example, the particles may comprise a biodegradable microparticle, such as a microsphere or nanosphere, and are capable of being injected or surgically placed within the anterior or posterior segment of the mammalian eye.

In a preferred embodiment, the MAA component is insoluble and forms a suspension of particles or crystals. In the case of very water-soluble MAA components such as oligonucleotides, charge complexation can be used to create such particles. For example, polycations such as polylysine or protamine can be used to form insoluble complexes with polyanions such as oligonucleotides. Macromolecular drugs in suspension are more likely to remain chemically stable during long-term storage than in aqueous solution.

In one embodiment, an intraocular drug delivery formulation comprises a therapeutic component comprising a non-neurotoxic macromolecule therapeutic agent and a viscosity inducing component. In certain embodiments the formulation may also contain a polymeric component associated with the therapeutic component to permit the therapeutic component to be released into the interior of an eye of an individual for at least about one week after the drug delivery system is placed in the eye.

In accordance with the present invention, the therapeutic component of the present systems can comprise, consist essentially of, or consist entirely of, anti-angiogenic agents, including neuroprotectant agents, or a combination of these. The therapeutic component may also comprise one or more of the following auxiliary therapeutic agents: bacteriocidal agents, growth factors, growth factor inhibitors, cytokines, intraocular pressure reducing agents, ocular hemorrhage therapeutic agents, and combinations thereof. In particularly preferred embodiments, the therapeutic component may comprise, consist essentially of, or consist of, a therapeutic agent selected from the group consisting of peptides, proteins, antibodies, antibody fragments, and nucleic acids. More specifically, the present formulations may comprise short interfering ribonucleic acids (siRNAs, also referred to as Sirnas), oligonucleotide aptamers, or VEGF or urokinase inhibitors. Some specific examples include one or more of the following: a hyaluronidase, such as Vitrase, (ocular hemorrhage treatment compound), ranibizumab (sold under the name LUCENTIS®), bevacizumab (sold under the name AVASTIN®), pegaptanib, such as MACUGEN®, (VEGF or VEGFR inhibitors), rapamycin, and cyclosporine. Advantageously, the therapeutic agent is available in a biologically active form when the present formulation is placed in an eye.

In one embodiment, the present compositions and methods may, without exception, comprise a MAAC which includes a macromolecule, such as a protein, peptide, (including modified protein or peptides and/or peptidomimetics) or a nucleic acid or modified nucleic acid, such as one containing modified nucleoside or ribonucleoside residues, or a peptide nucleic acid or other nucleic mimetic. Additionally, the MAAC may comprise an organic molecule other than a macromolecule; these organic, non-macromolecular MAACs shall be referred to herein as "small molecule components".

The viscosity-inducing component of the present compositions is present in an amount effective to increase the viscosity of the composition, which is usually an aqueous composition, preferably in fluid or gel form. Additionally, the viscosity-inducing component does not substantially denature or unfold the tertiary structure of the macromolecular component of the MAAC. The viscosity-inducing component is very preferably substantially or perfectly clear. In keeping with these guidelines, any suitable, ophthalmically acceptable, viscosity-inducing component may be employed in accordance with the present invention. Viscosity inducing components have been proposed, known, and/or used in ophthalmic compositions for treatment of the eye. Advantageously, the viscosity inducing component is present in an amount in a range of about 0.5% to about 20% (w/v) of the composition. In one particularly useful embodiment, the viscosity inducing component is a hyaluronic acid polymer component, such as sodium hyaluronate.

In a particularly preferred embodiment, the viscosity inducing component is substantially clear in solution, and present in an amount such that the refractive index of the resulting MAAC-containing composition is substantially similar to that of the vitreous humor, in order to prevent deleterious changes in vision after administration (such as intraocular delivery) of the composition to a patient. This is particularly desirable if the composition is injected into the posterior segment of the eye. In such cases, preferably the refractive index of the resulting MAAC-containing composition is substantially identical to that of the vitreous humor. However, these parameters may be less critical when the composition is administered by other means, e.g., by way of subconjuctival or subretinal delivery.

In one embodiment, the present compositions have a viscosity of at least about 10 cps or at least about 100 cps, preferably at least about 1,000 cps, more preferably at least about 10,000 cps and still more preferably at least about 70,000 cps, for example, up to about 250,000 cps, or about 300,000 cps, at a shear rate of 0.1/second at about 25° C. Preferably, the present compositions are structured or formulated to be effectively, for example, manually, injected into a posterior segment of an eye of a human or animal, preferably through a 27 gauge needle, more preferably through a 29 or 30 gauge needle.

Without wishing to limit the invention to any particular theory of operation, it is believed that the use of relatively high viscosity compositions, as described herein, provides for effective, and preferably substantially long-lasting delivery of the MAAC while, at the same time, being injectable into the posterior segment of an eye through conventionally, or even smaller than conventionally, used needles. In embodiments in which the MAAC is delivered in part as marginally or slowly soluble particles, the viscosity-inducing component is also effective to aid in keeping the particles in suspension, rather than being largely or mostly simply deposited on the bottom surface of the posterior segment of the eye.

In one embodiment of the invention, the MAAC is present in a plurality of particles which are substantially uniformly suspended in the composition and remain substantially uniformly suspended in the composition for at least about 1 week, preferably at least about 2 weeks or at least about 1 month, and still more preferably at least about 6 months or at least about 1 year or at least about 2 years, without requiring resuspension processing, that is, without requiring being shaken or otherwise agitated to maintain the MAAC particles substantially uniformly suspended in the composition.

Compositions having such substantially uniform suspension of MAAC particles, so as to be able to provide a consistent and accurate dose upon administration to an eye, provide substantial advantages relative to the prior art. In particular, the present compositions may be manufactured, shipped and stored for substantial periods of time without the MAAC particles precipitating from the remainder of the composition. Having the MAAC particles maintained substantially uniformly suspended in the composition allows the composition to provide long term dosing consistency and accuracy per unit dose amount administered, without any need to resuspend the MAAC particles.

The aqueous carrier component is advantageously ophthalmically acceptable and may include one or more conventional expedients useful in ophthalmic compositions. In one preferred and advantageous embodiment, the present compositions include no added preservative component. This feature reduces or minimizes or even substantially eliminates adverse reactions, such as cytotoxicity, in the eye which may be caused by or linked to the presence of a preservative component, particularly conventional preservatives such as benzalkonium chloride (known as BAC or BAK), and quaternary ammonium preservatives. In other embodiments, however, the carrier component may if desired include an effective amount of at least one of a preservative component, a tonicity component and/or a buffer component.

Methods of treating posterior segments of the eyes of humans or animals are also disclosed and are included within the scope of the present invention. In general, such methods comprise administering, e.g. injecting a MAAC-containing composition, for example, a composition in accordance with the present invention, to a posterior segment of an eye of a human or animal, such as into the vitreous humor of said eye. Such administering step is effective in providing a desired therapeutic effect to the tissues of the posterior segment. The administering step preferably comprises at least one of intravitreal injecting or placement, subconjunctival injecting or placement, sub-tenon injecting or placement, retrobulbar injecting or placement, suprachoroidal injecting or placement and the like.

The present invention encompasses a pharmaceutical composition for treating a posterior ocular condition, which term is defined below. The composition can comprise a MAAC; a viscosity inducing component in an amount effective to increase the viscosity of the composition, and; an aqueous carrier component. The composition can have a viscosity of at least about 10 cps at a shear rate of about 0.1/second and is injectable into the vitreous of a human eye, for example through a 27 gauge needle. By reducing the viscosity of our formulation it can be injected into the vitreous through a 28, 29, or 30 gauge needle.

The MAAC of the present pharmaceutical compositions comprise at least one macromolecular molecule that is either soluble, or is substantially uniformly suspended in the composition, and the viscosity inducing component is a polymeric hyaluronate.

A detailed embodiment within the scope of our invention is a pharmaceutical composition for treating a posterior ocular condition, comprising a MAAC; polymeric hyaluronate, in which the MAAC is present; sodium chloride; sodium phosphate, and water. The pharmaceutical composition can have a viscosity at a shear rate of about 0.1/second of between about 80,000 cps to about 300,000 cps, preferably from about 100,000 cps to about 300,000 cps, and most preferably from about 180,000 cps to about 225,000 cps. Note that the pharmaceutical composition can have a viscosity at a shear rate of about 0.1/second of between about 80,000 cps and about 300,000 cps, and that when the pharmaceutical composition has a viscosity at a shear rate of about 0.1/second of between about 100,000 cps and about 150,000 cps it can be injected into the vitreous through a 27, 28, 29, or 30 gauge needle. Even with a 300,000 cps it is believed the present formulations can be injected through a 30 gauge needle due to shear thinning once the formulation is in movement in the syringe. The sodium phosphate present in the pharmaceutical composition can comprise both monobasic sodium phosphate and dibasic sodium phosphate. Additionally, the pharmaceutical composition can comprise an effective dose of a MAAC, between about 2% w/v hyaluronate and about 3% w/v hyaluronate, about 0.6% w/v sodium chloride and between about 0.03% w/v sodium phosphate and about 0.04% w/v sodium phosphate. Alternately, the pharmaceutical composition of claim 5 can comprise between about 0.5% w/v hyaluronate and about 6% w/v hyaluronate. If desired the hyaluronate can be heated (see Example 15) to decrease its molecular weight (and therefore its viscosity) in the formulation.

The pharmaceutical composition can also comprises between about 0.6% w/v sodium chloride to about 0.9% w/v sodium chloride. Generally, more sodium chloride is used in the formulation as less phosphate is used in the formulation, for example 0.9% sodium chloride can be used if no phosphate is present in the formulation, as in this manner the tonicity of the formulation can be adjusted to obtain the desired isotonicity with physiological fluid. The pharmaceutical composition can comprise between about 0.0% w/v sodium phosphate and 0.1% w/v sodium phosphate. As noted, more phosphate can be used in the formulation if less sodium chloride is present in the formulation so as to obtain a desired pH 7.4 buffering effect.

Although hyaluronate solutions containing water-insoluble (or sparingly soluble) steroids or other compounds have been proposed for intravitreal injection (and in particular for a controlled delivery administration due to the particulate nature of the steroids), it has not been at all clear that intravitreally administered hyaluronate solutions would be useful for MAACs generally or any particular MAAC agent specifically. This is due in part to the limited maximum injection volume (about 100 µl) possible for intravitreal injection (which limits the maximum dosage possible), to the varying solubilities, chemistries, and specific activities of the various MAACs. Thus, for example, it is not obvious 1) any particular MAAC (including peptide and/or nucleic acid MAACs (including aptamers) would be soluble in HA, 2) for water soluble MAACs, that the advantages of HA as a carrier would pertain to a soluble molecule, 3) that any particular MAAC would be insoluble in HA to the extent that it is capable of being formulated in granular or particulate form with the requisite specific activity to make a MAAC-HA formulation medically advantageous, 4) that peptide or aptamer MAACs could be formulated to advantage in HA, and 5) with regard to specific MAAC compounds, that HA formulations combined with these particular compounds would be therapeutically efficacious, having a high enough specific activity for intravitreal administration.

A more detailed embodiment within the scope of our invention is a pharmaceutical composition for treating a posterior ocular condition, the pharmaceutical composition consisting essentially of a MAAC, polymeric hyaluronate, in which polymeric hyaluronate the MAAC is soluble, sodium chloride, sodium phosphate, and water. The pharmaceutical composition can have a viscosity at a shear rate 0.1/second of between about 128,000 cps and about 225,000 cps and the sodium phosphate present in the pharmaceutical composition can be present as both monobasic sodium phosphate and dibasic sodium phosphate.

A further embodiment of our invention is a MAAC formulation for treating a posterior ocular condition, consisting of a MAAC, polymeric hyaluronate, sodium chloride, dibasic sodium phosphate heptahydrate, monobasic sodium phosphate monohydrate, and water, wherein the composition has a viscosity at a shear rate 0.1/second of between about 128,000 cps and about 225,000 cps.

The invention also includes a method for treating a posterior ocular condition by administering (as by injecting) the pharmaceutical composition of claim 1 to the vitreous of a human or animal, thereby treating the posterior ocular condition. Thus, we have invented a method for treating macular edema, macular degeneration, diabetic retinopathy, and other intraocular diseases by administering to the vitreous of a human eye a pharmaceutical composition comprising a MAAC, and a hyaluronate, wherein the pharmaceutical composition having a viscosity at a shear rate 0.1/second of between about 128,000 cps and about 225,000 cps.

A pharmaceutical composition within the scope of our invention for treating a posterior ocular condition can, in certain embodiments, comprise a MAAC present in a therapeutically effective amount as a plurality of particles, a viscosity inducing component in an amount effective to increase the viscosity of the composition, and an aqueous carrier component, wherein the composition has a viscosity of at least about 10 cps at a shear rate of 0.1/second and is injectable into the vitreous of a human eye and wherein the pharmaceutical composition releases the MAAC slowly over a period of up to at least about 45 days after the intravitreal injection. This pharmaceutical composition can exhibit reduced generation of intraocular inflammation, no plume effect (that is no wide dispersion of the MAAC into the vitreous as soon as the MAAC is intravitreally injected), and cohesiveness (observed by the retention of the form of the MAAC gel for 30 weeks or longer after intravitreal injection of the MAAC gel formulation) upon intravitreal injection of the pharmaceutical composition.

Our invention encompasses a method for treating a posterior ocular condition, the method comprising the step of intravitreal administration of a sustained release pharmaceutical composition implant comprising a MAAC present in a therapeutically effective amount, a viscosity inducing component in an amount effective to increase the viscosity of the composition, and an aqueous carrier component, wherein the composition has a viscosity of at least about 10 cps at a shear rate of 0.1/second and is injectable into the vitreous of a human eye, and wherein the posterior ocular condition is treated for up to about 30 weeks by the MAAC of the present formulation. In this method the pharmaceutical composition can comprise a MAAC, polymeric hyaluronate, sodium chloride, sodium phosphate, and water. Additionally, the intravitreal administration can be injected through a 27 gauge needle into the vitreous of a human eye.

The invention also includes, when the MAAC is not entirely soluble in the aqueous carrier, a process for making a pharmaceutical composition by (a) mixing particles of the MAAC with sodium chloride crystals, and about 35% to about 40% of the total volume of the water (water for injection) used to make the formulation; (b) heating the MAAC and sodium chloride mixture to a temperature between about 20° C. and about 35° C., thereby preparing a first part; (c) mixing a sodium phosphate and water, thereby preparing a second part; (d) dissolving sodium hyaluronate with a molecular weight between about 1.0 million Daltons and about 1.9 million Daltons in another about 35% to about 40% of the total water volume used to make the formulation, followed by sterile filtration after the dissolving; (e) lyophilization of the dissolved sodium hyaluronate; (f) reconstitution of the lyophilized, sterile sodium hyaluronate, thereby preparing a third part; and; (g) aseptically combining the first, second and third parts, thereby making a sterile, uniform MAAC pharmaceutical composition which is, an opaque white gel suspension suitable for intravitreal injection to treat an ocular condition. Water is added as needed (q.s.) to make the desired gel suspension which is about 80% to about 90% by weight water.

BRIEF DESCRIPTION OF THE DRAWINGS

FIG. 1 is a chart aligning and comparing the amino acid sequences of the variable regions of bevacizumab and showing several similar amino acid sequences in such variable region, including the variable regions (heavy chain) of a) a murine monoclonal anti VEGF IGg1 antibody (SEQ ID NO: 16), b) a humanized F(ab) fragment having optimized VEGF binding (SEQ ID NO: 17) and c) the human consensus framework (SEQ ID NO: 18), as well as the variable regions (light chain) of d) a murine monoclonal anti VEGF IGg1 antibody (SEQ ID NO: 19), e) a humanized F(ab) fragment having optimized VEGF binding (SEQ ID NO: 20) and f) the human consensus framework (SEQ ID NO: 21).

DESCRIPTION

The present invention is based upon our discovery of MAAC-containing formulations specifically designed for intraocular, for example intravitreal, injection or administration to treat various ocular conditions, such a macula edema. Our MAAC formulations have numerous superior characteristics and advantages, including the following: (1) our formulations may be made to be free of preservatives and resuspension aids, such as benzyl alcohol and/or a polysorbate; (2) concomitantly, our formulations have a much reduced retinal and photoreceptor toxicity; (3) as well as being sterile and optionally preservative-free, our MAAC formulations can provide extended therapeutic effects due to the viscosity of the formulation and the relatively slow diffusion of the MAAC therefrom, and when formulated as a suspension of particles, can provide sustained release of therapeutic amounts of the MAAC over, for example, a period of months periods upon intravitreal injection of such formulations. Thus, our viscous MAAC formulations can be characterized as sustained release implants; (4) intravitreal administration of our MAAC formulations is substantially unassociated with an increased incidence of adverse events such as substantially elevated intraocular pressure, glaucoma, cataract and/an intraocular inflammation; (5) intravitreal administration of our MAAC formulations is not associated with an increased incidence of adverse events such elevated intraocular pressure, glaucoma, cataract and/an intraocular inflammation as compared to currently used or known intraocular (e.g., intravitreal) use MAAC formulations; (6) in certain embodiments, our formulations permit MAAC particles or crystals to be slowly released (as they solubilize in the viscous fluid of the posterior chamber) from a relatively discrete unitary location, thereby avoiding the plume effect (rapid dispersion) characteristic of less viscous aqueous formulations upon intravitreal administration; (7) avoidance of plume formation or rapid dispersion upon intravitreal administration, which beneficially reduces visual field obscuration.

Advantage (3) above can be provided by particular characteristics of our formulations, such as suspension of the MAAC in one or more particular high molecular weight polymers which permit sustained release of the MAAC by the formation of ion pairing or reverse phase association therewith. Thus, the MAAC is slowly related from its association with the gel.

Generally, the present invention provides compositions useful for placement, preferably by injection, into a posterior segment of an eye of a human or animal. Such compositions in the posterior, e.g., vitreous, of the eye are therapeutically effective against one or more conditions and/or diseases of the posterior of the eye, and/or one or more symptoms of such conditions and/or diseases of the posterior of the eye.

It is important to note that while preferably the compositions disclosed herein are preferably administered by intravitreal injection to treat a posterior ocular condition, our compositions can also be administered (as by injection) by other routes, such as for example subconjuctival, sub-tenon, periocular, retrobulbar, suprachoroidal, and/or intrascleral to effectively treat an ocular condition. Additionally, a sutured or refillable dome can be placed over the administration site to prevent or to reduce "wash out", leaching and/or diffusion of the active agent in a non-preferred direction.

Compositions within the scope of our invention can comprise a MAAC; a viscosity inducing component; and an aqueous carrier component. The compositions are advantageously ophthalmically acceptable. One of the important advantages of the present compositions is that they are more compatible with or less irritating or toxic to the tissues in the posterior segment of the eye, for example, the retina of the eye, relative to therapeutic compositions previously proposed for intravitreal injection into a posterior segment of an eye, for example, a composition sold under the trademark KENALOG®-40, which comprises the steroid triamcinolone. In particular, in certain embodiments the present compositions advantageously are substantially free of added preservative components or include effective preservative components which are more compatible with or less irritating or toxic to the posterior segment, e.g., retina, of the eye relative to benzyl alcohol, which is included in the KENALOG®-40 composition as a preservative.

As noted above, the present compositions include a MAAC. Such MAAC is present in the compositions in a therapeutically effective amount that is in an amount effective in providing a desired therapeutic effect in the eye into which the composition is placed. The MAAC is either soluble in the aqueous formulation or in certain embodiments is present in the composition in a plurality of particles. Any suitable MAAC may be employed in according to the present invention, provided it is at least sufficiently soluble in the vitreous humor to be able to administer a therapeutically effective dose to the ocular tissue.

In those embodiments in which the MAAC is not fully soluble in the formulation (and is present as a suspension of particles), certain parameters are helpfully observed. The MAAC of these embodiments advantageously has a limited solubility in water, for example, at 25° C. For example, the MAAC preferably has a solubility in water at 25° C. of less than 10 mg/ml. Of course, the MAAC should be ophthalmically acceptable, that is, should have substantially no significant or undue detrimental effect of the eye structures or tissues; of course this will depend upon the dosage regimen and the time period of continuous exposure of the tissues of the posterior segment. One particularly useful characteristic of the presently useful MAACs is the ability of such component to reduce the extent of angiogenesis, particularly VEGF-associated angiogenesis, in the posterior segment of the eye into which the composition is placed caused by the result of one or more diseases and/or conditions in the posterior segment of the eye.

The MAAC advantageously is present in an amount of at least about 10 mg per ml of the composition. Depending on the solubility of the MAAC, the MAAC may be present in the present compositions in an amount in the range of about 1% or less to about 5% or about 10% or about 20% or about 30% or more (w/v) of the composition, or about 0.2 mg per 100 µl or about 0.4 mg per 100 µl, or about 0.5 mg per 100 µl, or about 1.0 mg per 100 µl or about 2.0 mg per 100 µl, or about 4.0 mg per 100 µl, or about 5.0 mg per 100 µl, or about 6.0 mg per 100 µl, or about 7.0 mg per 100 µl, or about 8.0 mg per 100 µl, or about 10 mg per 100 µl, or about 20 mg per 100 µl, or about 40 mg per 100 µl, or about 60 mg per 100 µl, or about 80 mg per 100 µl. Providing relatively high concentrations or amounts of MAAC in the present compositions is beneficial in that reduced volumes and frequency of dosages of the composition may be required to be placed or injected into the posterior segment of the eye in order to provide the same amount or more MAAC in the posterior segment of the eye relative to compositions which include less than about 4% (w/v) of the MAAC. Thus, in one very useful embodiment, the present compositions include more than about 4% (w/v), for example at least about 5% (w/v), to about 10% (w/v) or about 20% (w/v) or about 30% (w/v) of the MAAC. Injection of 100 μL or more of a fluid into the vitreous can result in an excess of fluid in the vitreous with elevated intraocular pressure and leakage of the fluid from the vitreous then potentially occurring.

The viscosity inducing component is present in an effective amount in increasing, advantageously substantially increasing, the viscosity of the composition. Without wishing to limit the invention to any particular theory of operation, it is believed that increasing the viscosity of the compositions to values well in excess of the viscosity of water, for example, at least about 100 cps at a shear rate of 0.1/second, compositions which are highly effective for placement, e.g., injection, into the posterior segment of an eye of a human or animal are obtained. Along with the advantageous placement or injectability of the present compositions into the posterior segment, the relatively high viscosity of the present compositions are believed to enhance the ability of the present compositions to maintain the MAAC localized for a period of time within the posterior segment after intravitreal injection or placement. In the event that the composition comprises particles or crystals of the MAAC, the viscosity of the composition maintains the particles in substantially uniform suspension for prolonged periods of time, for example, for as long as 1 to 2 years, without requiring resuspension processing and thereby increasing the effective shelf life of the composition. The relatively high viscosity of the present compositions may also have an additional benefit of at least assisting the compositions to have the ability to have an increased amount or concentration of the MAAC, as discussed elsewhere herein.

Advantageously, the present compositions have viscosities of at least about 10 cps or at least about 100 cps or at least about 1000 cps, more preferably at least about 10,000 cps and still more preferably at least about 70,000 cps or more, for example up to about 200,000 cps or about 250,000 cps, or about 300,000 cps or more, at a shear rate of 0.1/second. The present compositions not only have the relatively high viscosity as noted above but also have the ability or are structured or formed to be effectively placeable, e.g., injectable, into a posterior segment of an eye of a human or animal, preferably through a 27 gauge needle, or even through a 30 gauge needle.

The presently useful viscosity inducing components preferably are shear thinning components in that as the present composition containing such a shear thinning viscosity inducing component is passed or injected into the posterior segment of an eye, for example, through a narrow space, such as 27 gauge needle, under high shear conditions the viscosity of the composition is substantially reduced during such passage. After such passage, the composition regains substantially its pre-injection viscosity.

Any suitable viscosity inducing component, for example, ophthalmically acceptable viscosity inducing component, may be employed in accordance with the present invention. Many such viscosity inducing components have been proposed and/or used in ophthalmic compositions used on or in the eye. The viscosity inducing component is present in an amount effective in providing the desired viscosity to the composition. Advantageously, (and depending on its properties and average molecular weight the viscosity inducing component is present in an amount in a range of about 0.5% or about 1.0% to about 5% or about 10% or about 20% (w/v) of the composition. The specific amount of the viscosity inducing component employed depends upon a number of factors including, for example and without limitation, the specific viscosity inducing component being employed, the molecular weight of the viscosity inducing component being employed, the viscosity desired for the present composition being produced and/or used and the like factors, such as shear thinning, biocompatibility and possible biodegradability of the compositions.

The viscosity inducing component preferably comprises a polymeric component and/or at least one viscoelastic agent, such as those materials which are useful in ophthalmic surgical procedures.

Examples of useful viscosity inducing components include, but are not limited to, hyaluronic acid (such as a polymeric hyaluronic acid), carbomers, polyacrylic acid, cellulosic derivatives, polycarbophil, polyvinylpyrrolidone, gelatin, dextrin, polysaccharides, polyacrylamide, polyvinyl alcohol, polyvinyl acetate, derivatives thereof and mixtures and copolymers thereof. In a particularly preferred embodiment the composition comprises a hyaluronic acid component, such as a polymeric hyaluronic acid component, including a cross-linked polymeric hyaluronic acid.

An average molecular weight of the presently useful viscosity inducing components may be in a range of about 10,000 Daltons or less to about 2 million Daltons or more. In one particularly useful embodiment, the molecular weight of the viscosity inducing component is in a range of about 100,000 Daltons or about 200,000 Daltons to about 1 million Daltons or about 1.5 million Daltons. Again, the molecular weight of the viscosity inducing component useful in accordance with the present invention, may vary over a substantial range based on the type of viscosity inducing component employed, and the desired final viscosity of the present composition in question, as well as, possibly one or more other factors. In one embodiment, two or more distinct molecular weight ranges of the viscosity inducing component may be used to increase the shear thinning attributes of the composition.

In one very useful embodiment, a viscosity inducing component is a polymeric hyaluronate component, for example, a metal hyaluronate component, preferably selected from alkali metal hyaluronates, alkaline earth metal hyaluronates and mixtures thereof, and still more preferably selected from sodium or potassium hyaluronates, and mixtures thereof. The molecular weight of such hyaluronate component (i.e. a polymeric hyaluronic acid) preferably is in a range of about 50,000 Daltons or about 100,000 Daltons to about 1.3 million Daltons or about 2 million Daltons. In one embodiment, the present compositions include a polymeric hyaluronate component in an amount in a range about 0.05% to about 0.5% (w/v). In a further useful embodiment, the hyaluronate component is present in an amount in a range of about 1% to about 4% (w/v) of the composition. In this latter case, the very high polymer viscosity forms a gel that slows particle sedimentation and diffusion of dissolved solutes upon injection in the eye. Such a composition may be marketed in pre-filled syringes since the gel cannot be easily removed by a needle and syringe from a bulk container. Pre-filled syringes have the advantages of convenience for the injector and the safety which results from less handling and the opportunity for error or contamination.

The aqueous carrier component is advantageously ophthalmically acceptable and may include one or more conventional excipients useful in ophthalmic compositions. The present compositions preferably include a major amount of liquid water. The present compositions may be, and are preferably, sterile, for example, prior to being used in the eye.

The present compositions preferably include at least one buffer component in an amount effective to control and/or maintain the pH of the composition and/or at least one tonicity component in an amount effective to control the tonicity or osmolality of the compositions; preferably the tonicity and/or osmolality will be substantially isotonic to the vitreous humor. More preferably, the present compositions include both a buffer component and a tonicity component.

The buffer component and tonicity component may be chosen from those which are conventional and well known in the ophthalmic art. Examples of such buffer components include, but are not limited to, acetate buffers, citrate buffers, phosphate buffers, borate buffers and the like and mixtures thereof. Phosphate buffers are particularly useful. Useful tonicity components include, but are not limited to, salts, particularly sodium chloride, potassium chloride, mannitol and other sugar alcohols, and other suitable ophthalmically acceptably tonicity component and mixtures thereof.

The amount of buffer component employed preferably is sufficient to maintain the pH of the composition in a range of about 6 to about 8, more preferably about 7 to about 7.5. The amount of tonicity component employed preferably is sufficient to provide an osmolality to the present compositions in a range of about 200 to about 400, more preferably about 250 to about 350, mOsmol/kg respectively. Advantageously, the present compositions are substantially isotonic.

The present compositions may include one or more other components in amounts effective to provide one or more useful properties and/or benefits to the present compositions. For example, although the present compositions may be substantially free of added preservative components, in other embodiments, the present compositions include effective amounts of preservative components, preferably such components which are more compatible with the tissue in the posterior segment of the eye into which the composition is placed than benzyl alcohol. Examples of such preservative components include, without limitation, benzalkonium chloride, chlorhexidine, PHMB (polyhexamethylene biguanide), methyl and ethyl parabens, hexetidine, chlorite components, such as stabilized chlorine dioxide, metal chlorites and the like, other ophthalmically acceptable preservatives and the like and mixtures thereof. The concentration of the preservative component, if any, in the present compositions is a concentration effective to preserve the composition, and is often in a range of about 0.00001% to about 0.05% or about 0.1% (w/v) of the composition.

In addition, if the MAAC is in suspension in the composition, the present composition may include an effective amount of resuspension component effective to facilitate the suspension or resuspension of the MAAC particles in the present compositions. As noted above, in certain embodiments, the present compositions are free of added resuspension components. In other embodiments of the present compositions effective amounts of resuspension components are employed, for example, to provide an added degree of insurance that the MAAC particles remain in suspension, as desired and/or can be relatively easily resuspended in the present compositions, such resuspension be desired. Advantageously, the resuspension component employed in accordance with the present invention, if any, is chosen to be more compatible with the tissue in the posterior segment of the eye into which the composition is placed than polysorbate 80.

Any suitable resuspension component may be employed in accordance with the present invention. Examples of such resuspension components include, without limitation, surfactants such as poloxanes, for example, sold under the trademark PLURONIC®; tyloxapol; sarcosinates; polyethoxylated castor oils, other surfactants and the like and mixtures thereof.

One very useful class of resuspension components are those selected from vitamin derivatives. Although such materials have been previously suggested for use as surfactants in ophthalmic compositions, they have been found to be effective in the present compositions as resuspension components. Examples of useful vitamin derivatives include, without limitation, Vitamin E tocopheryl polyethylene glycol succinates, such as Vitamin E tocopheryl polyethylene glycol 1000 succinate (Vitamin E TPGS). Other useful vitamin derivatives include, again without limitation, Vitamin E tocopheryl polyethylene glycol succinamides, such as Vitamin E tocopheryl polyethylene glycol 1000 succinamide (Vitamin E TPGSA) wherein the ester bond between polyethylene glycol and succinic acid is replaced by an amide group.

The presently useful resuspension components are present, if at all, in the compositions in accordance with the present invention in an amount effective to facilitate suspending the particles in the present compositions, for example, during manufacture of the compositions or thereafter. The specific amount of resuspension component employed may vary over a wide range depending, for example, on the specific resuspension component being employed, the specific composition in which the resuspension component is being employed and the like factors. Suitable concentrations of the resuspension component, if any, in the present compositions are often in a range of about 0.01% to about 5%, for example, about 0.02% or about 0.05% to about 1.0% (w/v) of the composition.

Solubility of the MAAC is clearly important to the effectiveness of the present MAAC-containing compositions, as is the potency and efficacy of the MAACs themselves. Very soluble MAACs are more readily and immediately available to the intraocular tissues, but may accordingly require smaller doses of the MAAC (and more frequent administration) to avoid substantially exceeding the effective dose. The viscosity of the present compositions will, to some extent, slow the diffusion of even these very soluble MAACs, but will not as effectively provide for an extended period of delivery and resulting efficacy as, for example is true when the MAAC is sequestered or somewhat insoluble (and thus solubilized over a period of time in situ) in the MAAC composition of the present invention. The availability of minimally soluble MAACs to intraocular tissues may be limited by the dissolution rate for these substances. As with readily soluble MAACs, slow dissolution is both good and bad for the patient. On the one hand, after a single intravitreal injection of the present composition, the mean elimination half-life for the MAAC is advantageously quite long. On the other hand, therapeutic drug levels in the vitreous compartment of the eye may not be achieved for some time (for example, about 1 to about 3 days), due to the slow dissolution rate of the MAAC particles.

In one embodiment of the present invention, for example, if a MAAC is not very soluble and particularly if the MAAC is both not very soluble and has a relatively high potency and/or efficacy, an effective amount of a solubilizing component is provided in the composition to solubilize a minor amount, that is less than 50%, for example in a range of 1% or about 5% to about 10% or about 20% of the MAAC. For example, the inclusion of a cyclodextrin component, such as β-cyclodextrin, sulfo-butylether β-cyclodextrin (SBE) other cyclodextrins and the like and mixtures thereof, at about 0.5 to about 5.0% (w/v) may solubilize about 1 to about 10% of the initial dose of the MAAC. This presolubilized fraction provides a readily bioavailable loading dose, thereby avoiding or minimizing delay time in achieving therapeutic effectiveness.

The use of such a solubilizing component is advantageous to provide any relatively quick "burst" release of an otherwise largely insoluble MAAC into the eye for therapeutic effectiveness. Such solubilizing component, of course, should be ophthalmically acceptable or at least sufficiently compatible with the posterior segment of the eye into which the composition is placed to avoid undue damage to the tissue in such posterior segment.

The pharmacokinetics of the MAAC following intravitreal administration may involve both the rate of drug dissolution and the rate of drug efflux via the anterior route. Patients typically require repeat dosing, for example about every two or three months, or otherwise as necessary.

In one embodiment of the present invention, the compositions further contain sustained release components, for example, polymers (in the form for example of gels and microspheres), such as poly (D,L,-lactide) or poly(D,L-lactide co-glycolide), in amounts effective to reduce local diffusion rates and/or MAAC particle dissolution rates. The result is a flatter elimination rate profile with a lower $C_{max}$ and a more prolonged therapeutic window, thereby extending the time between required injections for many patients.

Any suitable, preferably conditionally acceptable, release component may be employed. Useful examples are set forth above. The sustained release component is preferably biodegradable or bioabsorbable in the eye so that no residue remains over the long term. The amount of the delayed release component included may vary over a relatively wide range depending, for example, on the specific sustained release component is being employed, the specific release profile desired and the like factors. Typical amounts of delayed release components, if any, included in the present compositions are in a range of about 0.05 to 0.1 to about 0.5 or about 1 or more percent (w/v) (weight of the ingredient in the total volume of the composition) of the composition.

The present compositions can be prepared using suitable blending/processing techniques or techniques, for example, one or more conventional blending techniques. The preparation processing should be chosen to provide the present compositions in forms which are useful for placement or injection into the posterior segments of eyes of humans or animals. Soluble MAAC can be simply mixed with a hyaluronic acid solution. In one useful embodiment utilizing a somewhat insoluble MAAC, a MAAC dispersion is made by combining the MAAC with water, and the excipient (other than the viscosity inducing component) to be included in the final composition. The ingredients are mixed to disperse the MAAC and then autoclaved. Alternatively, the MAAC particles may be γ-irradiated before addition to the sterile carrier. The viscosity inducing component may be purchased sterile or sterilized by conventional processing, for example, by filtering a dilute solution followed by lyophylization to yield a sterile powder. The sterile viscosity inducing component is combined with water to make an aqueous concentrate. Under aseptic conditions, the concentrated MAAC dispersion can be blended or mixed and added or combined as a slurry to the viscosity inducing component concentrate. Water is added in a quantity sufficient (q.s.) to provide the desired composition and the composition is mixed until homogenous.

Methods of using the present composition are provided and are included within the scope of the present invention. In general, such methods comprise administering a composition in accordance with the present invention to a posterior segment of an eye of a human or animal, thereby obtaining a desired therapeutic effect, such as treatment of a given condition of the anterior or posterior segment of the eye. The administering step advantageously comprises at least one of intravitreal injecting, subconjunctival injecting, sub-tenon injecting, retrobulbar injecting, suprachoroidal injecting and the like. A syringe apparatus including an appropriately sized needle, for example, a 27 gauge needle or a 30 gauge needle, can be effectively used to inject the composition with the posterior segment of an eye of a human or animal.

Ocular conditions which can be treated or addressed in accordance with the present invention include, without limitation, the following:

Maculopathies/retinal degeneration: macular degeneration, including age related macular degeneration (ARMD), such as non-exudative age related macular degeneration and exudative age related macular degeneration, choroidal neovascularization, retinopathy, including diabetic retinopathy, acute and chronic macular neuroretinopathy, central serous chorioretinopathy, and macular edema, including cystoid macular edema, and diabetic macular edema. Uveitis/retinitis/choroiditis: acute multifocal placoid pigment epitheliopathy, Behcet's disease, birdshot retinochoroidopathy, infectious (syphilis, lyme, tuberculosis, toxoplasmosis), uveitis, including intermediate uveitis (pars planitis) and anterior uveitis, multifocal choroiditis, multiple evanescent white dot syndrome (MEWDS), ocular sarcoidosis, posterior scleritis, serpignous choroiditis, subretinal fibrosis, uveitis syndrome, and Vogt-Koyanagi-Harada syndrome. Vascular diseases/exudative diseases: retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemiretinal vein occlusion, papillophlebitis, central retinal artery occlusion, branch retinal artery occlusion, carotid artery disease (CAD), frosted branch angitis, sickle cell retinopathy and other hemoglobinopathies, angioid streaks, familial exudative vitreoretinopathy, Eales disease. Traumatic/surgical: sympathetic ophthalmia, uveitic retinal disease, retinal detachment, trauma, laser, PDT, photocoagulation, hypoperfusion during surgery, radiation retinopathy, bone marrow transplant retinopathy. Proliferative disorders: proliferative vitreal retinopathy and epiretinal membranes, proliferative diabetic retinopathy. Infectious disorders: ocular histoplasmosis, ocular toxocariasis, presumed ocular histoplasmosis syndrome (POHS), endophthalmitis, toxoplasmosis, retinal diseases associated with HIV infection, choroidal disease associated with HIV infection, uveitic disease associated with HIV Infection, viral retinitis, acute retinal necrosis, progressive outer retinal necrosis, fungal retinal diseases, ocular syphilis, ocular tuberculosis, diffuse unilateral subacute neuroretinitis, and myiasis. Genetic disorders: retinitis pigmentosa, systemic disorders with associated retinal dystrophies, congenital stationary night blindness, cone dystrophies, Stargardt's disease and fundus flavimaculatus, Bests disease, pattern dystrophy of the retinal pigmented epithelium, X-linked retinoschisis, Sorsby's fundus dystrophy, benign concentric maculopathy, Bietti's crystalline dystrophy, pseudoxanthoma elasticum. Retinal tears/holes: retinal detachment, macular hole, giant retinal tear. Tumors: retinal disease associated with tumors, congenital hypertrophy of the RPE, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, intraocular lymphoid tumors. Miscellaneous: punctate inner choroidopathy, acute posterior multifocal placoid pigment epitheliopathy, myopic retinal degeneration, acute retinal pigment epithelitis and the like.

The therapeutic component of the present drug delivery systems comprises one or more macromolecule therapeutic agents. Thus, the therapeutic component may be understood to comprise a MAAC. Examples of suitable macromolecule therapeutic agents include peptides, proteins, nucleic acids, antibodies, and antibody fragments. For example, the therapeutic component of the present drug delivery systems may comprise (without limitation), consist essentially of, or consist entirely of, one or more therapeutic agents selected from the group consisting of anti-angiogenesis compounds, ocular hemorrhage treatment compounds, macromolecular non-steroidal anti-inflammatory agents, growth factor inhibitors (e.g. VEGF inhibitors), growth factors, cytokines, antibodies, oligonucleotide aptamers, antisense oligonucleotides small interfering ribonucleic acid (siRNA) molecules and antibiotics. The present systems are effective to provide a therapeutically effective dosage(s) of the agent or agents directly to a region of the eye to treat, prevent, and/or reduce one or more symptoms of one or more undesirable ocular conditions. Thus, with each administration, therapeutic agents will be made available at the site where they are needed and will be maintained at effective concentrations for an extended period of time, rather than subjecting the patient to more frequent injections or, in the case of self-administered drops, ineffective treatment with only limited bursts of exposure to the active agent or agents or, in the case of systemic administration, higher systemic exposure and concomitant side effects or, in the case of non-sustained release dosages, potentially toxic transient high tissue concentrations associated with pulsed, non-sustained release dosing.

In a preferred embodiment the therapeutic components of the present invention may include polypeptide antibodies, antibody fragments, such as F(ab) and F(ab)' antibody fragments, recombinant antibody derivatives, and antibody mimics.

Antibody mimics may comprise an "addressable" region analogous to an antibody variable region, as with the fibronectin-based artificial antibodies discussed earlier. Antibody mimics such as these, which may advantageously have a decreased ability to stimulate an immune response, may be used in combination with the present systems to effectively to provide a therapeutically effective dosage(s) of the agent directly to a region of the eye to treat, prevent, and/or reduce one or more symptoms of one or more undesirable ocular conditions. Such an antibody mimic may, for example, be directed towards a ligand such as VEGF or a VEGFR receptor in a manner that causes binding of the antibody mimic and resultant neutralization of the activity of the ligand. In the case of VEGF, the antibody mimic may inhibit or lessen the angiogenic activity of VEGF and/or a VEGFR, such as VEGFR-1, or VEGF-2.

Examples of antibody mimics, and methods for constructing antibody mimics, are provided in, for example, et al., U.S. Pat. Nos. 6,818,418; 6,951,725; U.S. Patent Application Publication 2005/0074865 and U.S. Patent Application Publication No. 2004/0259155. Compound Therapeutics, Inc. have made and described a class of certain fibronectin based "addressable" therapeutic binding molecules they term "ADNECTINS®". Anti-VEGFR-2 ADNECTIN® compounds include CT-322, C7S100, and C7C100, which have all shown VEGFR-2 inhibitory activity in vitro and animal models, and the first of which is schedule to enter human clinical trials in 2006. See also, e.g., Mamluk et al., J. Clin. Oncol. 23:3150 (supp. Jun. 1, 2005). In preferred embodiments the antibody mimic may be PEGylated to increase its half life and decrease enzymatic digestion of the protein.

In another preferred embodiment, the present invention comprises an intraocular drug delivery system comprising a therapeutic component comprising an anti-angiogenic component and a viscosity-inducing component. Even more preferably, the present invention comprises at least a portion of a naturally occurring or synthetic antibody or antibody mimic having the ability to inhibit human VEGF activity. In one embodiment the antibody portion comprises an amino acid sequence comprising a contiguous sequence of at least 10, or at least 15, or at least 20 or at least 25 or at least 30, or at least 40 or at least 50 amino acids contained in the variable heavy sequences of FIG. 3 selected from the group consisting of A.4.6.1, F(ab)-12, and humIII. In another embodiment the antibody portion comprises an amino acid sequence comprising a contiguous sequence of at least 10, or at least 15, or at least 20 or at least 25 or at least 30, or at least 40 or at least 50 amino acids contained in the variable light sequences of FIG. 4 selected from the group consisting of A.4.6.1, F(ab)-12, and humk1.

In one specific embodiment the therapeutic component comprises a humanized anti-VEGF antibody, or fragment thereof, including a Fab fragment.

In another specific embodiment the therapeutic component comprises a contiguous sequence of at least 10, or at least 15, or at least 20 or at least 25 or at least 30, or at least 40 or at least 50 amino acids of the recombinant humanized anti-VEGF Fab fragment rambizumab (LUCENTIS®). In another specific embodiment the therapeutic component comprises a contiguous sequence of at least 10, or at least 15, or at least 20 or at least 25 or at least 30, or at least 40 or at least 50 amino acids of the recombinant humanized anti-VEGF IgG1 synthetic antibody bevacizumab (AVASTIN®). In an other specific embodiment, the therapeutic component separately comprises at least 10, or at least 15, or at least 20 or at least 25 or at least 30, or at least 40 or at least 50 contiguous amino acids of the amino acid sequence of ramizumab, and at least 10, or at least 15, or at least 20 or at least 25 or at least 30, or at least 40 or at least 50 contiguous amino acids of bevacizumab.

In certain embodiments, the therapeutic component of the present formulations comprises, consists essentially of, or consist of a short or small interfering ribonucleic acid (siRNA) or an oligonucleotide aptamer. For example, and in some preferred embodiments, the siRNA has a nucleotide sequence that is effective in inhibiting cellular production of vascular endothelial growth factor (VEGF) or VEGF receptors.

VEGF is an endothelial cell mitogen (Connolly D. T., et al., Tumor vascular permeability factor stimulates endothelial cell growth and angiogenesis. J. Clin. Invest. 84: 1470-1478 (1989)), that through binding with its receptor, VEGFR, plays an important role in the growth and maintenance of vascular endothelial cells and in the development of new blood- and lymphatic-vessels (Aiello L. P., et al., Vascular endothelial growth factor in ocular fluid of patients with diabetic retinopathy and other retinal disorders, New Engl. J. Med. 331: 1480-1487 (1994)).

Currently, the VEGF receptor family is believed to consist of three types of receptors, VEGFR-1 (Flt-1), VEGFR-2 (KDR/Flk-1) and VEGFR-3 (Flt-4), all of which belong to the receptor type tyrosine kinase superfamily (Mustonen T. et al., Endothelial receptor tyrosine kinases involved in angiogenesis, J. Cell Biol. 129: 895-898 (1995)). Among these receptors, VEGFR-1 appears to bind the strongest to VEGF, VEGFR-2 appears to bind more weakly than VEGFR-1, and VEGFR-3 shows essentially no binding, although it does bind to other members of the VEGF family. The tyrosine kinase domain of VEGFR-1, although much weaker than that of VEGFR-2, tranduces signals for endothelial cells. Thus, VEGF is a substance that stimulates the growth of new blood vessels. The development of new blood vessels, neovascularization or angiogenesis, in the eye is believed to cause loss of vision in wet macular degeneration and other ocular conditions, including edema.

In one embodiment, the present compositions may include active siRNA molecules can release effective amounts of active siRNA molecules that associate with a ribonuclease complex (RISC) in target cells to inhibit the production of a target protein, such as VEGF or VEGF receptors. The siRNA of the present systems can be double-stranded or single stranded RNA molecules and may have a length less than about 50 nucleotides. In certain embodiments, the systems may comprise a siRNA having a hairpin structure, and thus may be understood to be a short hairpin RNA (shRNA), as available from InvivoGen (San Diego, Calif.).

Some siRNAs that are used in the present systems preferably inhibit production of VEGF or VEGF receptors compared to other cellular proteins. In certain embodiments, the siRNAs can inhibit production of VEGF or VEGFR by at least 50%, preferably by at least 60%, and more preferably by about 70% or more. Thus, these siRNAs have nucleotide sequences that are effective in providing these desired ranges of inhibition.

In a particularly preferred embodiment the RNAi molecule comprises an siRNA oligonucleotide. In another preferred embodiment the siRNA is able to silence the expression of the VEGFR-2 receptor in a target cell. The antiVEGF-2 siRNA may comprise, for example, the following nucleotide sequences and their complementary oligonucleotide sequences, preferably their exact complements.

Examples of RNAi oligonucleotides directed against the VEGF-2 receptor may include siRNA Z, an siRNA therapeutic agent having silencing activity against VEGFR-1 and/or VEGFR-2, developed by SIRNA Therapeutics, Inc.

```
                                        SEQ ID NO: 22
     iB C U G A G U U U A A A A G G C A C C C TT iB

SEQ ID NO: 23
     TsT G A C U C A A A U U U U C C G U G G G
``` wherein iB is an inverted base, and TsT is a dithymidine dinucleotide segment linked by a phosphorothioate linkage. It is believed that each of these modifications adds to the nuclease resistance of the oligonucleotides. This and other relevant siRNA molecules are disclosed in e.g., U.S. Patent Publication 2005/0233344, which is hereby incorporated by reference herein in its entirety.

Essentially, siRNA Z is a modified short interfering RNA (siRNA) with an affinity for Vascular Endothelial Growth Factor Receptor-1 (VEGFR-1). VEGFR-1 has been located primarily on vascular endothelial cells and is stimulated by both VEGF and placental growth factor (PlGF), resulting in the growth of new blood vessels. By targeting VEGFR-1, siRNA Z can potentially down regulate activation of undesirable ocular angiogenesis influenced by VEGF and/or PlGF. General methods of making functional RNAi, and examples of specific siRNA are included in, for example, Kim et al., Am. J. Pathology 165:2177-2185 (2004); Tkaei et al., Cancer Res. 64:3365-3370 (May 15, 2004); Huh et al., Oncogene 24:790-800 (Jan. 27, 2005); WO 2003/070910; WO 2005/028649; WO 2005/044981; WO 2005/019453; WO 2005/0078097; WO 2003/070918; WO 2003/074654; WO 2001/75164; WO 2002/096927; U.S. Pat. Nos. 6,506,559; and 6,469,158, each of which references is hereby incorporated by reference herein in its entirety.

Additionally, the present invention also includes the use of proteins and nucleic acids therapeutic agents, such as antibodies, antibody mimics, and siRNA molecules that are capable of inhibiting the activity (including the expression and translation) of PDGF (platelet-derived growth factor). siRNAs directed against PDGF mRNA are disclosed in U.S. Patent Publication No. 2005/0233344, which is hereby incorporated by reference herein in its entirety.

The state of the art in gene silencing through siRNA has progressed to the point whereby computer algorithms are able to analyze a given mRNA or cDNA sequence and determine effective siRNA nucleotide sequences for the construction of oligonucleotides based upon such sequence. For example, Invitrogen Corp. offers a free Web-based tool called the BLOCK-IT™ RNAi Designer, in which a target mRNA is entered and will yield 10 high quality siRNA sequences. A list of the 10 highest quality inhibitors of human VEGF-2 based upon the BLOCK-IT™ RNAi Designer are below as SEQ ID NO: 1-SEQ ID NO: 10. Each of these oligonucleotides would preferably be used together with their complementary, preferably exactly complementary sequences.

```
gcgauggccucuucuguaa         SEQ ID NO: 1 ccaugucucggguccauuu         SEQ ID NO: 2 gcuuuacuauucccagcua         SEQ ID NO: 3 gggaauacccuucuucgaa         SEQ ID NO: 4 gcaucagcauaagaaacuu         SEQ ID NO: 5 gcugacauguacggucuau         SEQ ID NO: 6 ggaauugacaagacagcaa         SEQ ID NO: 7 ccacuuaccugaggagcaa         SEQ ID NO: 8 gcuccugaagaucuguaua         SEQ ID NO: 9 gcacgaaauauccucuuau         SEQ ID NO: 10
```

The nucleotide sequence of the human VEGF isoform, VEGF 165 is identified as SEQ ID NO: 11, below. The nucleotide sequence has a GenBank Accession Number AB021221.

```
                                                    (SEQ ID NO: 11)
     atgaactttctgctgtcttgggtgcattggagccttgccttgctgctctacctccacca tgccaagtggtcccaggctgcacccatggcagaaggagggggcagaatcatcacgaagtggtg aagttcatggatgtctatcagcgcagctactgccatccaatcgagaccctggtggacatcttcc
```

-continued

```
aggagtaccctgatgagatcgagtacatcttcaagccatcctgtgtgcccctgatgcgatgcgg gggctgctgcaatgacgagggcctggagtgtgtgcccactgaggagtccaacatcaccatgcag attatgcggatcaaacctcaccaaggccagcacataggagagatgagcttcctacagcacaaca aatgtgaatgcagaccaaagaaagatagagcaagacaagaaaatccctgtgggccttgctcaga gcggagaaagcatttgtttgtacaagatccgcagacgtgtaaatgttcctgcaaaaacacagac tcgcgttgcaaggcgaggcagcttgagttaaacgaacgtacttgcagatgtgacaagccgaggc ggtga
```

The nucleotide sequence of human VEGFR2 is identified as SEQ ID NO: 12, below. The nucleotide sequence has a GenBank Accession Number AF063658.

```
atggagagcaaggtgctgctggccgtcgccctgtggctctgcgtggagacccgggccgc ctctgtgggtttgcctagtgtttctcttgatctgcccaggctcagcatacaaaaagacatactt acaattaaggctaatacaactcttcaaattacttgcaggggacagagggacttggactggcttt ggcccaataatcagagtggcagtgagcaaagggtggaggtgactgagtgcagcgatggcctctt ctgtaagacactcacaattccaaaagtgatcggaaatgacactggagcctacaagtgcttctac cgggaaactgacttggcctcggtcatttatgtctatgttcaagattacagatctccatttattg cttctgttagtgaccaacatggagtcgtgtacattactgagaacaaaaacaaaactgtggtgat tccatgtctcgggtccatttcaaatctcaacgtgtcactttgtgcaagatacccagaaaagaga tttgttcctgatggtaacagaatttcctgggacagcaagaagggctttactattcccagctaca tgatcagctatgctggcatggtcttctgtgaagcaaaaattaatgatgaaagttaccagtctat tatgtacatagttgtcgttgtagggtataggatttatgatgtggttctgagtccgtctcatgga attgaactatctgttggagaaaagcttgtcttaaattgtacagcaagaactgaactaaatgtgg ggattgacttcaactgggaatacccttcttcgaagcatcagcataagaaacttgtaaaccgaga cctaaaaacccagtctgggagtgagatgaagaaattttttgagcaccttaactatagatggtgta acccggagtgaccaaggattgtacacctgtgcagcatccagtgggctgatgaccaagaagaaca gcacatttgtcagggtccatgaaaaacctttgttgcttttggaagtggcatggaatctctggt ggaagccacggtgggggagcgtgtcagaatccctgcgaagtaccttggttacccaccccagaa ataaaatggtataaaaatggaatacccttgagtccaatcacacaattaaagcggggcatgtac tgacgattatggaagtgagtgaaagagacacaggaaattacactgtcatccttaccaatcccat ttcaaaggagaagcagagccatgtggtctctctggttgtgtatgtcccacccccagattggtgag aaatctctaatctctcctgtggattcctaccagtacggcaccactcaaacgctgacatgtacgg tctatgccattcctccccgcatcacatccactggtattggcagttggaggaagagtgcgccaa cgagcccagccaagctgtctcagtgacaaacccataccccttgtgaagaatggagaagtgtggag gacttccagggaggaaataaaattgaagttaataaaaatcaatttgctctaattgaaggaaaaa acaaaactgtaagtacccttgttatccaagcggcaaatgtgtcagctttgtacaaatgtgaagc ggtcaacaaagtcgggagaggagagagggtgatctccttccacgtgaccaggggtcctgaaatt actttgcaacctgacatgcagcccactgagcaggagagcgtgtctttgtggtgcactgcagaca gatctacgtttgagaacctcacatggtacaagcttggcccacagcctctgccaatccatgtggg agagttgcccacacctgtttgcaagaacttggatactcttggaaattgaatgccaccatgttc tctaatagcacaaatgacattttgatcatggagcttaagaatgcatccttgcaggaccaaggag
```

-continued

```
actatgtctgccttgctcaagacaggaagaccaagaaaagacattgcgtggtcaggcagctcac agtcctagagcgtgtggcacccacgatcacaggaaacctggagaatcagacgacaagtattggg gaaagcatcgaagtctcatgcacggcatctgggaatcccctccacagatcatgtggtttaaag ataatgagaccccttgtagaagactcaggcattgtattgaaggatgggaaccggaacctcactat ccgcagagtgaggaaggaggacgaaggcctctacacctgccaggcatgcagtgttcttggctgt gcaaaagtggaggcattttttcataatagaaggtgcccaggaaaagacgaacttggaaatcatta ttctagtaggcacggcggtgattgccatgttcttctggctacttcttgtcatcatcctacggac cgttaagcgggccaatggaggggaactgaagacaggctacttgtccatcgtcatggatccagat gaactcccattggatgaacattgtgaacgactgccttatgatgccagcaaatgggaattcccca gagaccggctgaagctaggtaagcctcttggccgtggtgcctttggccaagtgattgaagcaga tgcctttggaattgacaagacagcaacttgcaggacagtagcagtcaaaatgttgaaagaagga gcaacacacagtgagcatcgagctctcatgtctgaactcaagatcctcattcatattggtcacc atctcaatgtggtcaaccttctaggtgcctgtaccaagccaggagggccactcatggtgattgt ggaattctgcaaatttggaaacctgtccacttacctgaggagcaagagaaatgaatttgtcccc tacaagaccaaaggggcacgattccgtcaagggaaagactacgttggagcaatccctgtggatc tgaaacggcgcttggacagcatcaccagtagccagagctcagccagctctggatttgtggagga gaagtccctcagtgatgtagaagaagaggaagctcctgaagatctgtataaggacttcctgacc ttggagcatctcatctgttacagcttccaagtggctaagggcatggagttcttggcatcgcgaa agtgtatccacagggacctggcggcacgaaatatcctcttatcggagaagaacgtggttaaaat ctgtgactttggcttggcccgggatatttataaagatccagattatgtcagaaaaggagatgct cgcctcccttttgaaatggatgccccagaaacaatttttgacagagtgtacacaatccagagtg acgtctggtcttttggtgttttgctgtgggaaatattttccttaggtgcttctccatatcctgg ggtaaagattgatgaagaatttttgtaggcgattgaaagaaggaactagaatgagggcccctgat tatactacaccagaaatgtaccagaccatgctggactgctggcacggggagcccagtcagagac ccacgttttcagagttggtggaacatttgggaaatctcttgcaagctaatgctcagcaggatgg caaagactacattgttcttccgatatcagagactttgagcatggaagaggattctggactctct ctgcctacctcacctgtttcctgtatggaggaggaggaagtatgtgaccccaaattccattatg acaacacagcaggaatcagtcagtatctgcagaacagtaagcgaaagagccggcctgtgagtgt aaaaacatttgaagatatcccgttagaagaaccagaagtaaaagtaatcccagatgacaaccag acggacagtggtatggttcttgcctcagaagagctgaaaactttggaagacagaaccaaattat ctccatcttttggtggaatggtgcccagcaaaagcagggagtctgtggcatctgaaggctcaaa ccagacaagcggctaccagtccggatatcactccgatgacacagacaccaccgtgtactccagt gaggaagcagaacttttaaagctgatagagattggagtgcaaaccggtagcacagcccagattc tccagcctgactcggggaccacactgagctctcctcctgtttaa
```

One specific example of a useful siRNA is available from Acuity Pharmaceuticals (Pennsylvania) or Avecia Biotechnology under the name Cand5. Cand5 is a therapeutic agent that essentially silences the genes that produce VEGF. Thus, drug delivery systems including an siRNA selective for VEGF can prevent or reduce VEGF production in a patient in need thereof. The nucleotide sequence of Cand5 is as follows.

The 5' to 3' nucleotide sequence of the sense strand of Cand5 is identified in SEQ ID NO:13 below.

ACCUCACCAAGGCCAGCACdTdT    (SEQ ID NO: 13)

The 5' to 3' nucleotide sequence of the anti-sense strand of Cand5 is identified in SEQ ID NO:14 below.

GUGCUGGCCUUGGUGAGGUdTdT    (SEQ ID NO: 14)

As mentioned above, another example of a useful siRNA is available from Sirna Therapeutics (Colorado) under the name siRNA Z. siRNA Z is a chemically modified short interfering RNA (siRNA) that targets vascular endothelial growth factor receptor-1 (VEGFR-1). Some additional examples of nucleic acid molecules that modulate the synthesis, expression and/or stability of an mRNA encoding one or more receptors of vascular endothelial growth factor are disclosed in U.S. Pat. No. 6,818,447 (Pavco), hereby incorporated by reference herein in its entirety).

Thus, the present drug delivery systems may comprise a MAAC that includes an siRNA having a nucleotide sequence that is substantially identical to the nucleotide sequence of Cand5 or siRNA Z, identified above. For example, the nucleotide sequence of a siRNA may have at least about 80% sequence homology to the nucleotide sequence of Cand5 or siRNA Z siRNAs. Preferably, a siRNA of the present invention has a nucleotide sequence homology of at least about 90%, and more preferably at least about 95% of the Cand5 or siRNA Z siRNAs. In other embodiments, the siRNA may have a homology to a VEGF mRNA or VEGFR mRNA isoform(s) that results in the inhibition or reduction of VEGF or VEGFR synthesis in the target tissue. Examples of anti-VEGFR oligonucleotides include those described in SEQ ID NO: 1-10 and 13 and 14 of this specification.

In another embodiment of the present viscous MAAC-containing formulations, the therapeutic component comprises an anti-angiogenic protein selected from the group consisting of endostatin (e.g., NCBI Accession Number AAK50626), angiostatin (e.g., NCBI Accession Number P00747), tumstatin (NCBI Accession Number AAF72632), pigment epithelium derived factor (e.g., NCBI Accession Number AAA84914), and VEGF TRAP (Regeneron Pharmaceuticals, New York). VEGF Trap is a fusion protein that contains portions of the extracellular domains of two different VEGF receptors connected to the Fc region (C-terminus) of a human antibody. Preparation of VEGF Trap is described in U.S. Pat. No. 5,844,099.

Other embodiments of the present systems may comprise an antibody selected from the group consisting of anti-VEGF antibodies, anti-VEGF receptor antibodies, anti-integrin antibodies, therapeutically effective fragments thereof, and combinations thereof.

Antibodies useful in the present systems include antibody fragments, such as Fab', F(ab)$_2$, Fabc, and Fv fragments. The antibody fragments may either be produced by the modification of whole antibodies or those synthesized de novo using recombinant DNA methodologies, and further include "humanized" antibodies made by now conventional techniques.

An antibody "specifically binds to" or "is immunoreactive with" a protein when the antibody functions in a binding reaction with the protein. The binding of the antibody to the protein may provide interference between the protein and its ligand or receptor, and thus the function mediated by a protein/receptor interaction can be inhibited or reduced. Several methods for determining whether or not a protein or peptide is immunoreactive with an antibody are known in the art. Immuno chemiluminescence metric assays (ICMA), enzyme-linked immunosorbent assays (ELISA) and radioimmunoassays (RIA) are some examples.

In certain specific embodiments, the present formulations may comprise a therapeutic component comprising a monoclonal antibody, fragment thereof, or recombinant polypeptide derived from an antibody variable region, or mixture thereof that interacts with (e.g., binds to and lessens or inhibits the activity of) VEGF. Monoclonal antibodies useful in the present ocular drug formulations can be obtained using routine methods known to persons of ordinary skill in the art. Briefly, animals such as mice are injected with a desired target protein or portion thereof, such as VEGF or VEGFR. The target protein is preferably coupled to a carrier protein. The animals are boosted with one or more target protein injections, and are hyperimmunized by an intravenous (IV) booster 3 days before fusion. Spleen cells from the mice are isolated and are fused by standard methods to myeloma cells. Hybridomas can be selected in standard hypoxanthine/aminopterin/thymine (HAT) medium, according to standard methods. Hybridomas secreting antibodies which recognize the target protein are identified, cultured, and subcloned using standard immunological techniques, and the antibody purified, for example, but affinity chromatography. In certain embodiments of the present systems, an anti-VEGF or anti-VEGFR monoclonal antibody is obtained from ImClone Systems, Inc. (NY, N.Y.). For example, the present formulations may include an antibody available from ImClone Systems under the name IMC-18F1 (icrucumab), or an antibody under the name of IMC-1121 Fab (ramucirumab). Another anti-VEGF antibody fragment that may be used in the present drug formulations is produced by Genentech and Novartis under the tradename LUCENTIS® (ranibizumab). LUCENTIS® is a derivative of the Genentech anti-VEGF antibody bevacizumab, approved to treatment of colorectal cancer and marketed as AVASTIN®.

In certain embodiments the present formulations may comprise an oligonucleotide aptamer that binds the 165-amino acid form of VEGF (VEGF 165). One example of a useful anti-VEGF aptamer is being produced by Eyetech Pharmaceuticals and Pfizer under the tradename MACUGEN® (pegaptanib sodium). MACUGEN® is marketed as an injectable liquid solution comprising a 3.47 mg/ml solution of 0.3 mg pegaptanib sodium in sodium chloride, mono- and dibasic sodium phosphate, and water. Aptamers may also be formulated that have an inhibitory effect against the VEGFR, such as VEGFR-2.

Another class of therapeutic agents useful in the formulations and methods of the present invention comprise VEGFR inhibitory antibody mimics, such as the VEGFR-2 inhibitors CT322, C7S100 and C7C100 made by Control Therapeutics, Inc. These antibody mimics comprise artificial antibodies built using a fibronectin scaffold also with an "addressable" region that selectively binds a given ligand in a manner similar to the variable region of an antibody. These artificial antibodies have the added advantage of being capable to being designed to be less immunogenic than antibodies.

In addition or alternatively, the present systems may comprise a peptide that inhibits a urokinase. For example, the peptide may have 8 amino acids and is effective in inhibiting the urokinase plasminogen activator, uPA. Urokinase plasminogen activator is often observed to be overexpressed in many types of human cancer. Thus, the present systems which comprise a urokinase inhibitor can effectively treat cancer and metastasis, as well as reduce tumor growth, such as ocular tumor growth. One example of a urokinase peptide inhibitor is known as A6, which is derived from a nonreceptor binding region of uPA and includes amino acids 136-143 of uPA.

The sequence of A6 is Ac-KPSSPPEE-amide (SEQ ID NO:15).

Certain of the present formulations can include a combination of A6 and cisplatin and effectively reduce neovascularization in the eye. Additional peptides may have similar amino acid sequences such that the peptides have a similar inhibiting activity as A6. For example, the peptides may have conservative amino acid substitutions. Peptides that have at least 80% homology, and preferably at least about 90% homology to A6 may provide the desired inhibition of uPA.

The present systems may also comprise rapamycin (sirolimus). Rapamycin is a peptide that functions as an antibiotic, an immunosuppressive agent, and an anti-angiogenic agent. Rapamycin can be obtained from A.G. Scientific, Inc. (San Diego, Calif.). Synergistic therapeutic effects may be achieved upon use of a rapmycin formulation comprising a viscosity-inducing component for intraocolar administration. Rapamycin may be understood to be an immunosuppressive agent, an anti-angiogenic agent, a cytotoxic agent, or combinations thereof. The chemical formula of rapamycin is $C_{51}H_{79}NO_{13}$ and it has a molecular weight of 914.18. Rapamycin has been assigned the CAS Registry Number 53123-88-9. Rapamycin-containing drug formulations may provide effective treatment of one or more ocular conditions by interfering with a T-cell mediated immune response, and/or causing apoptosis in certain cell populations of the eye. Thus, rapamycin-containing drug formulations can provide effective treatment of one or more ocular conditions, such as uveitis, macular degeneration including age related macular degeneration, and other posterior ocular conditions. It has been discovered that by incorporating a peptide, such as rapamycin, into the present formulations, therapeutically effective amounts of rapamycin can be provided in the interior of an eye with reduced side effects that may be associated with other forms of delivery, including intravitreal injection of non-viscous liquid formulations and transscleral delivery. For example, the present formulations may have one or more reduced side effects, such as a reduction in one or more of the following: raised lipid and cholesterol levels, hypertension, anaemia, diarrhea, rash, acne, thrombocytopenia, and decreases in platelets and haemoglobin. Although these side effects may be commonly observed upon systemic administration of rapamycin, one or more of these side effects can be observed upon ocular administration as well. U.S. Patent Publication No. 2005/0064010 (Cooper et al.) discloses transcleral delivery of therapeutic agents to ocular tissues.

In addition, rapamycin-containing viscous anti-angiogenic formulations may also be used in combination with other anti-inflammatory agents, including steroidal and non-steroidal anti-inflammatory agents, other anti-angiogenic agents, and other immunosuppressive agents. Such combination therapies can be achieved by providing more than one type of therapeutic agent in the present ocular formulations, by administering two or more viscous drug delivery formulations containing two or more types of therapeutic agents, or by administering a rapamycin-containing viscous formulation with an ophthalmic composition containing one or more other therapeutic agents. A combination therapy approach can include placement of a drug delivery system that comprises injecting a viscous formulation comprising rapamycin and triamcinolone acetonide in the vitreous of an eye. Other approaches can include intraocular administration of the present viscous anti-angiogenic formulations that comprise rapamycin and tacrolimus, rapamycin and methotrexate, and other anti-inflammatory agents. In addition to the foregoing, the present drug delivery systems can include other limus compounds, such as cyclophins and FK506-binding proteins, everolimus, pimecrolimus, CCI-779 (Wyeth), AP23841 (Ariad), and ABT-578 (Abbott Laboratories). Additional limus compound analogs and derivatives useful in the present implants include those described in U.S. Pat. Nos. 5,527,907; 6,376,517; and 6,329,386; and U.S. Publication No. 20020123505.

In short, a MAAC of the present viscous intraocular compositions may include organic molecules capable of modulating, regulating and/or inhibiting angiogenesis.

The present compounds may also include salts of the MAACs. Pharmaceutically acceptable acid addition salts of the compounds of the invention are those formed from acids which form non-toxic addition salts containing pharmaceutically acceptable anions, such as the hydrochloride, hydrobromide, hydroiodide, sulfate, or bisulfate, phosphate or acid phosphate, acetate, maleate, fumarate, oxalate, lactate, tartrate, citrate, gluconate, saccharate and p-toluene sulphonate salts.

Thus, the formulation of the present invention may comprise a MAAC which comprises, consists essentially of, or consists of a MAAC, salts thereof, and mixtures thereof.

Additional MAACs may be obtained or synthesized using conventional methods, such as by routine chemical synthesis and recombinant DNA, polymerase chain reaction, and protein expression methods known to persons of ordinary skill in the art. See e.g., Sambrook & Russell, MOLECULAR CLONING: A LABORATORY MANUAL (3d ed. Cold Spring Harbor Laboratory Press 2001), hereby incorporated by reference in its entirety. Therapeutically effective MAACs may be screened and identified using conventional screening technologies used for the MAACs described herein.

The MAACs may be in a soluble form, or in a particulate or powder form in suspension in the present formulations.

The MAAC of the present formulations is preferably from about 10% to 90% by weight of the compositions. More preferably, the MAAC is from about 20% to about 80% by weight of the composition. In a preferred embodiment, the MAAC comprises about 40% by weight of the composition (e.g., 30%-50%). In another embodiment, the MAAC comprises about 60% by weight of the composition. In yet another embodiment of the invention, the MAAC comprises about 0.2 mg per 100 µl or about 0.4 mg per 100 µl, or about 0.5 mg per 100 µl, or about 1.0 mg per 100 µl or about 2.0 mg per 100 µl, or about 4.0 mg per 100 µl, or about 5.0 mg per 100 µl, or about 6.0 mg per 100 µl, or about 7.0 mg per 100 µl, or about 8.0 mg per 100 µl, or about 10 mg per 100 µl, or about 20 mg per 100 µl, or about 40 mg per 100 µl, or about 60 mg per 100 µl, or about 80 mg per 100 µl.

When referring to a peptide having a particular amino acid sequence or a nucleic acid having a nucleotide sequence in this patent application, it will be understood that said protein or nucleic acid may containing a region having at least 80% identity to said sequence, or at least 85% identity to said sequence, or at least 90% identity to said sequence, or at least 95% identity to said sequence, or at least 98% identity to said sequence, or 100% identity to said sequence.

In addition to the MAAC(s) included in the present intraocular formulations, the intraocular formulations may also include one or more additional ophthalmically acceptable therapeutic agents. For example, the composition may include one or more antihistamines, one or more antibiotics, one or more beta blockers, one or more alpha 2 adrenergic receptor agonist, one or more steroids, one or more antineoplastic agents, one or more immunosuppressive agents, one or more antiviral agents, one or more antioxidant agents, and mixtures thereof.

Examples of antihistamines include, and are not limited to, loradatine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, dexbrompheniramine, methdilazine, and trimprazine doxylamine, pheniramine, pyrilamine, chlorcyclizine, thonzylamine, and derivatives thereof.

Examples of antibiotics include without limitation, cefazolin, cephradine, cefaclor, cephapirin, ceftizoxime, cefoperazone, cefotetan, cefutoxime, cefotaxime, cefadroxil, ceftazidime, cephalexin, cephalothin, cefamandole, cefoxitin, cefonicid, ceforanide, ceftriaxone, cefadroxil, cephradine, cefuroxime, cyclosporine, ampicillin, amoxicillin, cyclacillin, ampicillin, penicillin G, penicillin V potassium, piperacillin, oxacillin, bacampicillin, cloxacillin, ticarcillin, azlocillin, carbenicillin, methicillin, nafcillin, erythromycin, tetracycline, doxycycline, minocycline, aztreonam, chloramphenicol, ciprofloxacin hydrochloride, clindamycin, metronidazole, gentamicin, lincomycin, tobramycin, vancomycin, polymyxin B sulfate, colistimethate, colistin, azithromycin, augmentin, sulfamethoxazole, trimethoprim, gatifloxacin, ofloxacin, and derivatives thereof.

Examples of beta blockers include acebutolol, atenolol, labetalol, metoprolol, propranolol, timolol, and derivatives thereof.

Examples of alpha 2 adrenergic receptor agonists include, without limitation brimonidine and clonidine.

Examples of steroids include corticosteroids, such as cortisone, prednisolone, fluorometholone, dexamethasone, medrysone, loteprednol, fluazacort, hydrocortisone, prednisone, betamethasone, prednisone, methylprednisolone, riamcinolone hexacatonide, paramethasone acetate, diflorasone, fluocinonide, fluocinolone, triamcinolone, derivatives thereof, and mixtures thereof.

Examples of antineoplastic agents include adriamycin, cyclophosphamide, actinomycin, bleomycin, duanorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxol and derivatives thereof, taxotere and derivatives thereof, vinblastine, vincristine, tamoxifen, etoposide, piposulfan, cyclophosphamide, and flutamide, and derivatives thereof.

Examples of immunosuppressive agents include cyclosporine, azathioprine, tacrolimus, and derivatives thereof.

Examples of antiviral agents include interferon gamma, zidovudine, amantadine hydrochloride, ribavirin, acyclovir, valciclovir, dideoxycytidine, phosphonoformic acid, ganciclovir and derivatives thereof.

Examples of antioxidant agents include ascorbate, alpha-tocopherol, mannitol, reduced glutathione, various carotenoids, cysteine, uric acid, taurine, tyrosine, superoxide dismutase, lutein, zeaxanthin, cryotpxanthin, astazanthin, lycopene, N-acetyl-cysteine, carnosine, gamma-glutamyl-cysteine, quercitin, lactoferrin, dihydrolipoic acid, citrate, *Ginkgo Biloba* extract, tea catechins, bilberry extract, vitamins E or esters of vitamin E, retinyl palmitate, and derivatives thereof.

Other therapeutic agents include squalamine, carbonic anhydrase inhibitors, alpha agonists, prostamides, prostaglandins, antiparasitics, antifungals, and derivatives thereof.

The amount of active agent or agents employed in the implant, individually or in combination, will vary widely depending on the effective dosage required and the desired rate of release from the implant. As indicated herein, the agent will be at least about 1, more usually at least about 10 weight percent of the implant, and usually not more than about 80, more usually not more than about 40 weight percent of the compositions.

The present implants are configured to release an amount of the MAAC(s) effective to treat or reduce a symptom of an ocular condition, such as an ocular condition.

The viscous formulations disclosed herein may also be configured to release the antiexcitotoxic agent(s) or additional therapeutic agents, as described above, which to prevent diseases or conditions, such as the following:

Glaucoma, maculopathies/retinal degeneration: macular degeneration, including age related macular degeneration (ARMD), such as non-exudative age related macular degeneration and exudative age related macular degeneration, choroidal neovascularization, retinopathy, including diabetic retinopathy, acute and chronic macular neuroretinopathy, central serous chorioretinopathy, and macular edema, including cystoid macular edema, and diabetic macular edema.

Uveitis/retinitis/choroiditis: acute multifocal placoid pigment epitheliopathy, Behcet's disease, birdshot retinochoroidopathy, infectious (syphilis, lyme, tuberculosis, toxoplasmosis), uveitis, including intermediate uveitis (pars planitis) and anterior uveitis, multifocal choroiditis, multiple evanescent white dot syndrome (MEWDS), ocular sarcoidosis, posterior scleritis, serpignous choroiditis, subretinal fibrosis, uveitis syndrome, and Vogt-Koyanagi-Harada syndrome.

Vascular diseases/exudative diseases: retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angitis, sickle cell retinopathy and other hemoglobinopathies, angioid streaks, familial exudative vitreoretinopathy, Eales disease.

Traumatic/surgical: sympathetic ophthalmic, uveitic retinal disease, retinal detachment, trauma, laser, PDT, photocoagulation, hypoperfusion during surgery, radiation retinopathy, bone marrow transplant retinopathy.

Proliferative disorders: proliferative vitreal retinopathy and epiretinal membranes, proliferative diabetic retinopathy.

Infectious disorders: ocular histoplasmosis, ocular toxocariasis, presumed ocular histoplasmosis syndrome (POHS), endophthalmitis, toxoplasmosis, retinal diseases associated with HIV infection, choroidal disease associated with HIV infection, uveitic disease associated with HIV Infection, viral retinitis, acute retinal necrosis, progressive outer retinal necrosis, fungal retinal diseases, ocular syphilis, ocular tuberculosis, diffuse unilateral subacute neuroretinitis, and myiasis.

Genetic disorders: retinitis pigmentosa, systemic disorders with associated retinal dystrophies, congenital stationary night blindness, cone dystrophies, Stargardt's disease and fundus flavimaculatus, Bests disease, pattern dystrophy of the retinal pigmented epithelium, X-linked retinoschisis, Sorsby's fundus dystrophy, benign concentric maculopathy, Bietti's crystalline dystrophy, pseudoxanthoma elasticum.

Retinal tears/holes: retinal detachment, macular hole, giant retinal tear.

Tumors: retinal disease associated with tumors, congenital hypertrophy of the RPE, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, intraocular lymphoid tumors.

Miscellaneous: punctate inner choroidopathy, acute posterior multifocal placoid pigment epitheliopathy, myopic retinal degeneration, acute retinal pigment epithelitis and the like.

In one embodiment, a viscous formulation comprising a MAAC, such as the formulations disclosed herein, is administered to a posterior segment of an eye of a human or animal patient, and preferably, a living human or animal. In at least one embodiment, an viscous MAAC-containing formulation of the present invention is administered (e.g., injected), into the subretinal space of the eye. In other embodiments, a method of treating a patient may include placing the MAAC containing composition of the present invention directly into the posterior chamber of the eye. In other embodiments, a method of treating a patient may comprise administering the composition to the patient by at least one of intravitreal injection, subconjuctval injection, sub-tenon injections, retrobulbar injection, and suprachoroidal injection.

In at least one embodiment, a method of improving vision or maintaining vision in a patient comprises administering a composition containing one or more MAAC, as disclosed herein to a patient by at least one of intravitreal injection, subconjunctival injection, sub-tenon injection, retrobulbar injection, and suprachoroidal injection. A syringe apparatus including an appropriately sized needle, for example, a 22 gauge needle, a 27 gauge needle or a 30 gauge needle, can be effectively used to inject the composition with the posterior segment of an eye of a human or animal.

In another aspect of the invention, kits for treating an ocular condition of the eye are provided, comprising: a) a container comprising an extended release composition comprising a therapeutic component including a MAAC in a viscous carrier; and b) instructions for use. Such a kit may comprise a pre-loaded syringe ready for injection.

EXAMPLES

The following non-limiting Examples are presented to exemplify aspects of the present invention.

Example 1

Intravitreal Pharmacokinetics of MAACs in Fluid Compositions

The ocular pharmacokinetics of ranibizumab (Lucentis®; rhuFab V2e) (COMPOUND A); bevacizumab (Avastin®; rhuMab-VEGF) (COMPOUND B); pegaptanib (MACUGEN®) (COMPOUND C); and siRNA Z (a short interfering RNA (siRNA) directed against either or both the VEGF-1 or VEGF-2 receptors) (COMPOUND D) following single intravitreal injections into female albino rabbit eyes is determined. The animals are dosed with a 100 µL intravitreal aqueous saline injection of 10 µg of each compound. Vitreous humor samples (n=4 eyes per timepoint) are collected at 0.5, 1, 2, 4, 8, and 12 hr postdose. The concentration of each MAAC in the vitreous humor is determined using a liquid chromatography tandem mass spectrometry method (LC-MS/MS). All compounds tested are eliminated fairly rapidly from the rabbit eye, with the polypeptide MAACs generally having a longer half-life in the posterior chamber than the nucleic acid siRNA Z. Based on the data obtained in this study it is determined that local sustained delivery of each MAAC is feasible. Based on the vitreal clearance determined in this study and assuming steady state efficacious concentration at twice the $EC_{50}$ values (which may be determined by in vitro receptor binding and intracellular $Ca^{2+}$ assay), these compounds could be successfully formulated for intraocular delivery.

Examples 2 to 8

Eight compositions are as follows:

TABLE 1

| Ingredient | Example 1 | Example 2 | Example 3 | Example 4 |
|---|---|---|---|---|
| COMPOUND A | 0.5 mg | 1 mg | | |
| Sodium Hyaluronate (average molecular weight $0.6 \times 10^6$ DALTONS) | 0.05% (w/v) | 0.5% (w/v) | 0.05% (w/v) | 0.5% (w/v) |
| Sodium Phosphate | 0.4% (w/v) | 0.4% (w/v) | 0.4% (w/v) | 0.4% (w/v) |
| Vitamin E-TPGS | 0.5% (w/v) | 0.5% (w/v) | 0.0 | 0.0 |
| COMPOUND B | | | 0.5 mg | 1 mg |
| Water for Injection | q.s. | q.s. | q.s. | q.s. |
| Viscosity (at 25° C.) at shear rate 0.1/second | 20 cps | 500 cps | 20 cps | 500 cps |

TABLE 4

| Ingredient | Example 5 | Example 6 | Example 7 | Example 8 |
|---|---|---|---|---|
| COMPOUND C | 0.5 mg | 1 mg | | |
| Sodium Hyaluronate (average molecular weight $0.6 \times 10^6$ DALTONS) | 0.05% (w/v) | 0.5% (w/v) | 0.05% (w/v) | 0.5% (w/v) |
| Sodium Phosphate | 0.4% (w/v) | 0.4% (w/v) | 0.4% (w/v) | 0.4% (w/v) |
| Vitamin E-TPGS | 0.5% (w/v) | 0.5% (w/v) | 0.0 | 0.0 |
| COMPOUND D | | | 0.5 mg | 1 mg |
| Water for Injection | q.s. | q.s. | q.s. | q.s. |
| Viscosity (at 25° C.) at shear rate 0.1/second | 20 cps | 500 cps | 20 cps | 500 cps |

Each of these compositions is prepared as follows.

A concentrated solution of each MAAC is made by combining the MAAC with water, and Vitamin E-TPGS. These ingredients are mixed and then filter sterilized. The sodium hyaluronate may be purchased as a sterile powder or sterilized by filtering a dilute solution followed by lyophylization to yield a sterile powder. The sterile sodium hyaluronate is dissolved in water to make an aqueous concentrate of at least twice the desired final concentration. Each concentrated MAAC solution is mixed and added to the sodium hyaluronate concentrate, with stirring. Water is added q.s. (quantum sufficit, as much as suffices, in this case as much as is required to prepare the concentration of the solution, gel or suspension) and the mixture is then mixed until homogenous.

These compositions can be marketed in small volume pharmaceutical grade glass bottles or plastic syringes, and are found to be therapeutically effective as a therapeutic agent for the treatment of conditions of the posterior segment of the eye, including age-related macular degeneration and diabetic retinopathy when injected intravitreally into human eyes.

Examples 9 to 11

Three compositions are as follows:

TABLE 5

| Ingredient | Example 9 | Example 10 | Example 11 |
|---|---|---|---|
| COMPOUND A | 0.5 mg | 1.0 mg | 2.0 mg |
| Sodium hyaluronate | 3.0% (w/v) | 2.5% (w/v) | 2.0% (w/v) |
| Sodium Phosphate | 0.4% (w/v) | 0.4% (w/v) | 0.4% (w/v) |
| Water for Injection | q.s. | q.s. | q.s. |
| Viscosity (at 25° C.) at shear rate 0.1/second | 300,000 cps | 180,000 cps | 100,000 cps |

These compositions are prepared in a manner substantially analogous to that set forth in Example 2.

The high viscosities of the compositions substantially slows the diffusion rate of the MAAC when administered into the eye such as by intravitreal injection. These compositions can be marketed in prefilled syringes since they can not easily be removed by a needle and syringe from a container. However, with the compositions in prefilled syringes, the compositions can be effectively injected into the posterior segment of an eye of a human using a 27 gauge or a 30 gauge needle to provide a desired therapeutic effect in the human eye.

The compositions of Examples 9 to 11 employ or contain a sufficient concentration of high molecular weight sodium hyaluronate so as to form a gelatinous plug or drug depot upon intravitreal injection into a human eye.

Examples 12 and 13

Two compositions are as follows:

TABLE 3

| Ingredient | Example 12 | Example 13 |
|---|---|---|
| COMPOUND D | 0.5 mg | 1 mg |
| Sodium hyaluronate (polymeric) | 2.5% (w/v) | 2.3% (w/v) |
| Sodium chloride | 0.63% (w/v) | 0.63% (w/v) |
| dibasic sodium phosphate, heptahydrate | 0.30% (w/v) | 0.30% (w/v) |
| Monobasic sodium phosphate, monohydrate | 0.04% (w/v) | 0.04% (w/v) |
| Water for Injection | q.s. | q.s. |
| Viscosity (at 25° C.) at shear rate 0.1/second | 170,000 ± 25% cps | 200,000 ± 25% cps |

These compositions are prepared in a manner substantially analogous to that set forth in Example 2.

These compositions can be marketed in prefilled syringes since they can not easily be removed by a needle and syringe from a container. However, with the compositions in prefilled syringes, the compositions can be effectively injected into the posterior segment of an eye of a human using a 27 gauge or a 30 gauge needle to provide a desired therapeutic effect in the human eye.

The sodium hyaluronate powders used in these compositions (as well as in the other compositions identified in the Examples herein) have water contents in a range of about 4% to about 20%, preferably about 4% to about 8%, by weight. Differences in the average molecular weight of the hyaluronate used can result in variation in the viscosity of compositions in accordance with the present invention such that the compositions have the same nominal chemical make-ups. Thus, the viscosities indicated herein should be understood to be target viscosities, with the composition being acceptable for use if the actual viscosity of the composition is within plus or minus (±.) about 25% or about 30% or about 35% of the target viscosity.

Because each of the compositions set forth in the Examples has a density of about 1 gm/ml, the percentages set forth herein as being based on weight per volume (w/v) can also be considered as being based on weight per weight (w/w).

The compositions of Examples 1-13 employ or contain a sufficient concentration of high molecular weight (i.e. polymeric) sodium hyaluronate so as to form a gelatinous plug or drug depot upon intravitreal injection into a human eye.

Preferably the average molecular weight of the hyaluronate used is less than about 2 million, and more preferably the average molecular weight of the hyaluronate used is between about 1.3 million and 1.6 million. Since sodium hyaluronate solutions are subject to dramatic shear thinning, these formulations are easily injected through 27 gauge or even 30 gauge needles.

The Example 1-13 formulations can be used to treat, for example, exudative macular degeneration, diabetic retinopathy, macular edema, central retinal vein occlusion, and branch retinal vein occlusion. Notable these formulations are made using only excipients that are ophthalmically acceptable; that is, compatible (i.e. non-toxic) to the eye, particularly to the retina.

Example 14

Treatment of Macular Edema with Intravitreal MAAC Composition

A 64 year old obese female patient with symptoms of diabetes presents with vision loss due to macula edema with central retinal vein occlusion and/or branch retinal vein occlusion. She receives intravitreal injection of 1 mg of a high viscosity MAAC (polymeric hyaluronate based) solution containing COMPOUND D, such as the Example 13 formulation. Equivalent injections are made every 4 months.

Twelve months after the first injection the patient demonstrates an improved best corrected visual acuity of fifteen or more letters from baseline as determined using the Early Treatment of Diabetic Retinopathy Study (ETDRS) visual acuity chart.

Example 15

Treatment of a Posterior Ocular Condition with Intravitreal Ranibizumab High Viscosity Composition Patients with a posterior ocular condition (such as a macular edema, uveitis, or macular degeneration) can be treated by intravitreal injection of 1 mg or 2 mg of a MAAC in a high viscosity gel (polymeric hyaluronate based) containing COMPOUND A, substantially similar to that of the Example 12 or 13 formulation. Alternately, the formulation can be administered by subconjunctival injection to treat the posterior ocular condition. These patients can demonstrate 3 months or more after injection an improved best corrected visual acuity of fifteen or more letters from baseline as determined using the Early Treatment of Diabetic Retinopathy Study (ETDRS) visual acuity chart.

Example 16

Treatment of Macular Degeneration with Intravitreal Bevacizumab (AVASTIN®) in a High Viscosity Gel A 79 year-old male presents with significant visual distortion and loss; retinal examination reveals an exudative coroidal neovacularization in the region of the macula of both eyes. The patient is given a topical dose of an ocular hypotensive agent, and then an intravitreal injection of a viscous composition of 1 mg bevacizumab in 2% polyhyaluronic acid prepared (except for the active agent) in a manner similar to the composition used in Example 15 in the left eye. The right eye is not treated. Follow-up injections are made in an identical manner every 6 weeks for a period of 52 weeks.

At the end of the treatment period the patient's rate of vision loss is approximately 0.125 letters per week in the treated eye, versus about 0.5 letter per week in the untreated eye.

Example 17

Treatment of Diabetic Retinopathy with High Viscosity ADNECTIN® CT-322

A 50 year old man suffering from chronic, alcohol-aggravated diabetic retinopathy is administered a high viscosity composition comprising 2 mg of a PEGylated ADNECTIN® CT-322 preparation containing 2% (w/v) sodium hyaluronate, prepared substantially as indicated in Example 15, by intravitreal injection. Prior to treatment vision loss progresses at a rate of 0.4 letter per week in each eye. Treatment is repeated every six weeks for 52 weeks. The patient is tested 56 weeks following the initiation of the treatment. Vision loss is less than 8 letters over 56 weeks.

While this invention has been described with respect to various specific examples and embodiments, it is to be understood that the invention is not limited thereto. Each and every one of the references, articles, nucleotide or amino acid sequences referred to by accession numbers, publications, patents and applications set forth above is hereby expressly incorporated herein by reference in its entirety.

We claim:

1. A method for treating a posterior ocular condition, the method comprising:
    administering into the vitreous of an eye of a mammal suffering from an ocular condition a composition consisting of;
    a therapeutically effective amount of a macromolecular anti-angiogenic component (MAAC), wherein the MAAC is selected from a VEGF antibody comprising bevacizumab, a VEGF antibody fragment comprising ranibizumab, a VEGF antibody mimic comprising CT-322, C7S100, or C7C100, and combinations thereof;
    a viscosity inducing component in an amount effective to increase the viscosity of the composition to a viscosity at about 25° C. of at least 10 cps at a shear rate of about 0.1/second, wherein said viscosity inducing component is injectable into the vitreous of a mammalian eye without permanently diminishing visual acuity,
    sodium chloride,
    dibasic sodium phosphate heptahydrate, monobasic sodium phosphate monohydrate, and
    water;
    wherein the posterior ocular condition is selected from macular edema, macular degeneration, diabetic retinopathy, and combinations thereof; and
    wherein the administering is by subconjunctival, suprachoroidal, intravitreal or combination thereof.

2. The method of claim 1 wherein said viscosity inducing component comprises a compound having a molecular weight in the range from about 10,000 Daltons to about 2 million Daltons.

3. The method of claim 1 wherein said viscosity inducing component comprises a compound having a molecular weight in the range of about 100,000 Daltons to about 1.5 million Daltons.

4. The method of claim 1 wherein said viscosity inducing component comprises a compound having a molecular weight in the range of about 200,000 Daltons to about 1 million Daltons.

5. The method of claim 1 wherein said viscosity inducing component has a viscosity of at least 100 cps at a shear rate of 0.1/second at 25° C.

6. The method of claim 1 wherein said viscosity inducing component has a viscosity of at least 1000 cps at a shear rate of 0.1/second at 25° C.

7. The method of claim 1 wherein said viscosity inducing component has a viscosity of at least 10,000 cps at a shear rate of 0.1/second at 25° C.

8. The method of claim 1 wherein said viscosity inducing component has a viscosity of at least 70,000 cps at a shear rate of 0.1/second at 25° C.

9. The method of claim 1 wherein said viscosity inducing component has a viscosity of at least 200,000 cps at a shear rate of 0.1/second at 25° C.

10. The method of claim 1 wherein said viscosity inducing component has a viscosity of at least 250,000 cps at a shear rate of 0.1/second at 25° C.

11. The method of claim 1 wherein said viscosity inducing component has a viscosity of at least 300,000 cps at a shear rate of 0.1/second at 25° C.

12. The method of claim 1 wherein said composition is administered to the vitreous of said eye by placement into the vitreous of the eye through a 27-gauge needle.

13. The method of claim 1 wherein said composition is administered to the vitreous of said eye by placement into the vitreous of the eye through a 30-gauge needle.

14. A method for treating a posterior ocular condition, the method comprising:
    administering into the vitreous of an eye of a mammal suffering from an ocular condition a composition consisting of;
    a therapeutically effective amount of a MAAC selected from one or more of: a VEGF TRAP; icrucumab, ramucirumab, endostatin, angiostatin, tumstatin, and pigment epithelium derived factor,
    a viscosity inducing component in an amount effective to increase the viscosity of the composition to a viscosity at about 25° C. of at least 10 cps at a shear rate of about 0.1/second, wherein said viscosity inducing component is injectable into the vitreous of a mammalian eye without permanently diminishing visual acuity, sodium chloride, dibasic sodium phosphate heptahydrate, monobasic sodium phosphate monohydrate, and water;

wherein the posterior ocular condition is selected from macular edema, macular degeneration, diabetic retinopathy, and combinations thereof; and wherein the administering is by subconjunctival, suprachoroidal, intravitreal or combination thereof.

* * * * *

SEQUENCE LISTING

```
<160> NUMBER OF SEQ ID NOS: 23

<210> SEQ ID NO 1
<211> LENGTH: 19
<212> TYPE: RNA
<213> ORGANISM: Artificial Sequence
<220> FEATURE:
<223> OTHER INFORMATION: software-predicted inhibitors of human VEGF2

<400> SEQUENCE: 1
gcgauggccu cuucuguaa                                                    19

<210> SEQ ID NO 2
<211> LENGTH: 19
<212> TYPE: RNA
<213> ORGANISM: Artificial Sequence
<220> FEATURE:
<223> OTHER INFORMATION: Software-prediected inhibitor of human VEGF-2

<400> SEQUENCE: 2
ccaugucucg gguccauuu                                                    19

<210> SEQ ID NO 3
<211> LENGTH: 19
<212> TYPE: RNA
<213> ORGANISM: Artificial sequence
<220> FEATURE:
<223> OTHER INFORMATION: Software predicted inhibitOr of human VEGF-2

<400> SEQUENCE: 3
gcuuuacuau ucccagcua                                                    19

<210> SEQ ID NO 4
<211> LENGTH: 19
<212> TYPE: RNA
<213> ORGANISM: Artificial sequence
<220> FEATURE:
<223> OTHER INFORMATION: software-predicted inhibitor of VEGF-2

<400> SEQUENCE: 4
gggaauaccc uucuucgaa                                                    19
```

```
<210> SEQ ID NO 5
<211> LENGTH: 19
<212> TYPE: RNA
<213> ORGANISM: Artificial sequence
<220> FEATURE:
<223> OTHER INFORMATION: software-predicted inhibitor of human VEGF-2

<400> SEQUENCE: 5
gcaucagcau aagaaacuu                                                 19

<210> SEQ ID NO 6
<211> LENGTH: 19
<212> TYPE: RNA
<213> ORGANISM: Artificial sequence
<220> FEATURE:
<223> OTHER INFORMATION: software-predicted inhibitor of human VEGF-2

<400> SEQUENCE: 6
gcugacaugu acggucuau                                                 19

<210> SEQ ID NO 7
<211> LENGTH: 19
<212> TYPE: RNA
<213> ORGANISM: Artificial Sequence
<220> FEATURE:
<223> OTHER INFORMATION: software-predicted inhibitor of human VEGF-2

<400> SEQUENCE: 7
ggaauugaca agacagcaa                                                 19

<210> SEQ ID NO 8
<211> LENGTH: 19
<212> TYPE: RNA
<213> ORGANISM: Artificial Sequence
<220> FEATURE:
<223> OTHER INFORMATION: software -predicted inhibitor of human VEGF-2

<400> SEQUENCE: 8
ccacuuaccu gaggagcaa                                                 19

<210> SEQ ID NO 9
<211> LENGTH: 19
<212> TYPE: RNA
<213> ORGANISM: Artificial sequence
<220> FEATURE:
<223> OTHER INFORMATION: software-predicted inhibitor of human VEGF-2

<400> SEQUENCE: 9
gcuccugaag aucuguaua                                                 19

<210> SEQ ID NO 10
<211> LENGTH: 19
<212> TYPE: RNA
<213> ORGANISM: Artificial sequence
<220> FEATURE:
<223> OTHER INFORMATION: software-predicted inhibitor of human VEGF-2

<400> SEQUENCE: 10
gcacgaaaua uccucuuau                                                 19

<210> SEQ ID NO 11
<211> LENGTH: 576
<212> TYPE: DNA
<213> ORGANISM: Homo sapiens

<400> SEQUENCE: 11
```

| | |
|---|---:|
| atgaactttc tgctgtcttg ggtgcattgg agccttgcct tgctgctcta cctccaccat | 60 |
| gccaagtggt cccaggctgc acccatggca aaggaggag ggcagaatca tcacgaagtg | 120 |
| gtgaagttca tggatgtcta tcagcgcagc tactgccatc caatcgagac cctggtggac | 180 |
| atcttccagg agtaccctga tgagatcgag tacatcttca agccatcctg tgtgcccctg | 240 |
| atgcgatgcg ggggctgctg caatgacgag ggcctggagt gtgtgcccac tgaggagtcc | 300 |
| aacatcacca tgcagattat gcggatcaaa cctcaccaag gccagcacat aggagagatg | 360 |
| agcttcctac agcacaacaa atgtgaatgc agaccaaaga agatagagc aagacaagaa | 420 |
| aatccctgtg gccttgctc agagcggaga aagcatttgt ttgtacaaga tccgcagacg | 480 |
| tgtaaatgtt cctgcaaaaa cacagactcg cgttgcaagg cgaggcagct tgagttaaac | 540 |
| gaacgtactt gcagatgtga caagccgagg cggtga | 576 |

<210> SEQ ID NO 12
<211> LENGTH: 4071
<212> TYPE: DNA
<213> ORGANISM: Homo sapiens

<400> SEQUENCE: 12

| | |
|---|---:|
| atggagagca aggtgctgct ggccgtcgcc ctgtggctct gcgtggagac ccgggccgcc | 60 |
| tctgtgggtt tgcctagtgt ttctcttgat ctgcccaggc tcagcataca aaaagacata | 120 |
| cttacaatta aggctaatac aactcttcaa attacttgca ggggacagag ggacttggac | 180 |
| tggcttttggc ccaataatca gagtggcagt gagcaaaggg tggaggtgac tgagtgcagc | 240 |
| gatggcctct tctgtaagac actcacaatt ccaaaagtga tcggaaatga cactggagcc | 300 |
| tacaagtgct tctaccggga aactgacttg gcctcggtca tttatgtcta tgttcaagat | 360 |
| tacagatctc catttattgc ttctgttagt gaccaacatg gagtcgtgta cattactgag | 420 |
| aacaaaaaca aaactgtggt gattccatgt ctcgggtcca tttcaaatct caacgtgtca | 480 |
| ctttgtgcaa gataccccaga aaagagattt gttcctgatg gtaacagaat ttcctgggac | 540 |
| agcaagaagg gctttactat tcccagctac atgatcagct atgctggcat ggtcttctgt | 600 |
| gaagcaaaaa ttaatgatga agttaccag tctattatgt acatagttgt cgttgtaggg | 660 |
| tataggatt atgatgtggt tctgagtccg tctcatggaa ttgaactatc tgttggagaa | 720 |
| aagcttgtct taaattgtac agcaagaact gaactaaatg tggggattga cttcaactgg | 780 |
| gaataccctt cttcgaagca tcagcataag aaacttgtaa accgagacct aaaaacccag | 840 |
| tctgggagtg agatgaagaa attttttgagc accttaacta tagatggtgt aaccccggagt | 900 |
| gaccaaggat tgtacacctg tgcagcatcc agtgggctga tgaccaagaa gaacagcaca | 960 |
| tttgtcaggg tccatgaaaa acctttttgtt gcttttggaa gtggcatgga atctctggtg | 1020 |
| gaagccacgg tggggagcg tgtcagaatc cctgcgaagt accttggtta cccacccca | 1080 |
| gaaataaaat ggtataaaaa tggaatacccc cttgagtcca atcacacaat taaagcgggg | 1140 |
| catgtactga cgattatgga agtgagtgaa agagacacag gaaattacac tgtcatcctt | 1200 |
| accaatccca tttcaaagga gaagcagagc catgtggtct ctctggttgt gtatgtccca | 1260 |
| ccccagattg tgagaaatc tctaatctct cctgtggatt cctaccagta cggcaccact | 1320 |
| caaacgctga catgtacggt ctatgccatt cctcccccgc atcacatcca ctggtattgg | 1380 |
| cagttggagg aagagtgcgc caacgagccc agccaagctg tctcagtgac aaacccatac | 1440 |
| ccttgtgaaa atggagaag tgtggaggac ttccaggga gaaataaaat tgaagttaat | 1500 |
| aaaaatcaat ttgctctaat tgaaggaaaa aacaaaactg taagtaccct tgttatccaa | 1560 |

```
gcggcaaatg tgtcagcttt gtacaaatgt gaagcggtca acaaagtcgg gagaggagag    1620
agggtgatct ccttccacgt gaccagsggt cctgaaatta ctttgcaacc tgacatgcag    1680
cccactgagc aggagagcgt gtctttgtgg tgcactgcag acagatctac gtttgagaac    1740
ctcacatggt acaagcttgg cccacagcct ctgccaatcc atgtgggaga gttgcccaca    1800
cctgtttgca agaacttgga tactctttgg aaattgaatg ccaccatgtt ctctaatagc    1860
acaaatgaca ttttgatcat ggagcttaag aatgcatcct gcaggacca aggagactat     1920 gtctgccttg ctcaagacag gaagaccaag aaaagacatt gcgtggtcag gcagctcaca    1980
gtcctagagc gtgtggcacc cacgatcaca ggaaacctgg agaatcagac acaagtatt     2040 ggggaaagca tcgaagtctc atgcacggca tctgggaatc cccctccaca gatcatgtgg    2100
tttaaagata tgagaccct tgtagaagac tcaggcattg tattgaagga tgggaaccgg    2160
aacctcacta tccgcagagt gaggaaggag gacgaaggcc tctacacctg ccaggcatgc    2220
agtgttcttg ctgtgcaaa agtggaggca ttttcataa tagaaggtgc ccaggaaaag     2280
acgaacttgg aaatcattat tctagtaggc acggcggtga ttgccatgtt cttctggcta    2340
cttcttgtca tcatcctacg gaccgttaag cgggccaatg gagggaact gaagacaggc     2400 tacttgtcca tcgtcatgga tccagatgaa ctcccattgg atgaacattg tgaacgactg    2460
ccttatgatg ccagcaaatg ggaattcccc agagaccggc tgaagctagg taagcctctt    2520
ggccgtggtg cctttggcca agtgattgaa gcagatgcct ttggaattga caagacagca    2580
acttgcagga cagtagcagt caaaatgttg aaagaaggag caacacacag tgagcatcga    2640
gctctcatgt ctgaactcaa gatcctcatt catattggtc accatctcaa tgtggtcaac    2700
cttctaggtg cctgtaccaa gccaggaggg ccactcatgg tgattgtgga attctgcaaa    2760
tttggaaacc tgtccactta cctgaggagc aagagaaatg aatttgtccc ctacaagacc    2820 aaagggcac gattccgtca agggaaagac tacgttggag caatccctgt ggatctgaaa    2880
cggcgcttgg acagcatcac cagtagccag agctcagcca gctctggatt tgtggaggag    2940
aagtccctca gtgatgtaga agaagaggaa gctcctgaag atctgtataa ggacttcctg    3000
accttggagc atctcatctg ttacagcttc caagtggcta agggcatgga gttcttggca    3060
tcgcgaaagt gtatccacag ggacctggcg gcacgaaata tcctcttatc ggagaagaac    3120
gtggttaaaa tctgtgactt tggccttggcc cgggatattt ataaagatcc agattatgtc    3180
agaaaaggag atgctcgcct cccctttgaaa tggatggccc cagaaacaat ttttgacaga    3240
gtgtacacaa tccagagtga cgtctggtct tttggtgttt tgctgtggga aatattttcc    3300
ttaggtgctt ctccatatcc tgggtaaag attgatgaag aattttgtag gcgattgaaa    3360
gaaggaacta gaatgagggc ccctgattat actacaccag aaatgtacca gaccatgctg    3420
gactgctggc acgggagcc agtcagaga cccacgtttt cagagttggt ggaacatttg    3480
ggaaatctct tgcaagctaa tgctcagcag gatggcaaag actacattgt tcttccgata    3540
tcagagactt tgagcatgga gaggattct ggactctctc tgcctacctc acctgtttcc     3600
tgtatggagg aggaggaagt atgtgacccc aaattccatt atgacaacac agcaggaatc    3660
agtcagtatc tgcagaacag taagcgaaag agccggcctg tgagtgtaaa acatttgaa     3720 gatatcccgt tagaagaacc agaagtaaaa gtaatcccag atgacaacca gacggacagt    3780
ggtatggttc ttgcctcaga agagctgaaa actttggaag acagaaccaa attatctcca    3840
tcttttggtg aatggtgcc cagcaaaagc agggagtctg tggcatctga aggctcaaac    3900
```

```
cagacaagcg gctaccagtc cggatatcac tccgatgaca cagacaccac cgtgtactcc    3960
agtgaggaag cagaactttt aaagctgata gagattggag tgcaaaccgg tagcacagcc    4020
cagattctcc agcctgactc ggggaccaca ctgagctctc ctcctgttta a             4071
```

<210> SEQ ID NO 13
<211> LENGTH: 21
<212> TYPE: DNA
<213> ORGANISM: Artificial sequence
<220> FEATURE:
<223> OTHER INFORMATION: inhibitor of human VEGF

<400> SEQUENCE: 13

```
accucaccaa ggccagcact t                                               21
```

<210> SEQ ID NO 14
<211> LENGTH: 21
<212> TYPE: DNA
<213> ORGANISM: Artificial sequence
<220> FEATURE:
<223> OTHER INFORMATION: inhibitor of human VEGF

<400> SEQUENCE: 14

```
accucaccaa ggccagcact t                                               21
```

<210> SEQ ID NO 15
<211> LENGTH: 8
<212> TYPE: PRT
<213> ORGANISM: Artificial sequence
<220> FEATURE:
<223> OTHER INFORMATION: inhibitor of human unokinase

<400> SEQUENCE: 15

Lys Pro Ser Ser Pro Pro Glu Glu
1               5

<210> SEQ ID NO 16
<211> LENGTH: 123
<212> TYPE: PRT
<213> ORGANISM: Unknown
<220> FEATURE:
<223> OTHER INFORMATION: mouse anti-VEGF antibody variable region from
      heavy chain

<400> SEQUENCE: 16

Glu Ile Gln Leu Val Gln Ser Gly Pro Glu Leu Lys Gln Pro Gly Glu
1               5                   10                  15

Thr Val Arg Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Glu Thr Ser Ala Ser Thr Ala Tyr
65                  70                  75                  80

Leu Gln Ile Ser Asn Leu Lys Asn Asp Asp Thr Ala Thr Tyr Phe Cys
                85                  90                  95

Ala Lys Tyr Pro His Tyr Tyr Gly Ser Ser His Trp Tyr Phe Asp Val
            100                 105                 110

Trp Gly Ala Gly Ile Thr Val Thr Val Ser Ser
        115                 120

<210> SEQ ID NO 17
<211> LENGTH: 123
<212> TYPE: PRT
<213> ORGANISM: Unknown
<220> FEATURE:
<223> OTHER INFORMATION: Humanized mouse anti-VEGF antibody variable
      region (heavy chain)

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 18
<211> LENGTH: 113
<212> TYPE: PRT
<213> ORGANISM: Unknown
<220> FEATURE:
<223> OTHER INFORMATION: Human consensus framework (variable region of
      antibody heavy chain)

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Cys Leu Glu Trp Val
        35                  40                  45

Ser Val Ile Ser Gly Asp Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Phe Asp Tyr Trp Gly Gln Gly Thr Leu Val Thr Val Ser
            100                 105                 110

Ser

<210> SEQ ID NO 19
<211> LENGTH: 108
<212> TYPE: PRT
<213> ORGANISM: Unknown
<220> FEATURE:
<223> OTHER INFORMATION: anti-VEGF murine mAb (variable region of light
      chain)

<400> SEQUENCE: 19

```
Asp Ile Gln Met Thr Gln Thr Ser Ser Leu Ser Ala Ser Leu Gly
1               5                   10                  15

Asp Arg Val Ile Ile Ser Cys Ser Ala Ser Gln Asp Ile Ser Asn Tyr
            20                  25                  30

Leu Asn Trp Tyr Gln Gln Lys Pro Asp Gly Thr Val Lys Val Leu Ile
            35                  40                  45

Tyr Phe Thr Ser Ser Leu His Ser Gly Val Pro Ser Arg Phe Ser Gly
            50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Thr Val Phe Trp
                85                  90                  95

Thr Phe Gly Gly Gly Thr Lys Leu Glu Ile Lys Arg
            100                 105
```

<210> SEQ ID NO 20
<211> LENGTH: 108
<212> TYPE: PRT
<213> ORGANISM: Unknown
<220> FEATURE:
<223> OTHER INFORMATION: Humanized anti-VEGF F(ab) (variable region of
      light chain)

<400> SEQUENCE: 20

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
            35                  40                  45

Tyr Phe Thr Ser Ser Leu His Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg
            100                 105
```

<210> SEQ ID NO 21
<211> LENGTH: 108
<212> TYPE: PRT
<213> ORGANISM: Unknown
<220> FEATURE:
<223> OTHER INFORMATION: human consensus framework (variable region of
      light chain)

<400> SEQUENCE: 21

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Ala Trp Tyr Gln Gln Lys Pro Gly Lys Ala Pro Lys Leu Leu Thr
            35                  40                  45

Tyr Ala Ala Ser Ser Leu Glu Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Tyr Asn Ser Leu Pro Trp
                85                  90                  95

Thr Phe Gly Gln Gly Thr Lys Val Glu Ile Lys Arg
            100                 105

<210> SEQ ID NO 22
<211> LENGTH: 21
<212> TYPE: DNA
<213> ORGANISM: Artificial sequence
<220> FEATURE:
<223> OTHER INFORMATION: inhibior of human  VEGFR-1 and VEGFR-2

<400> SEQUENCE: 22
cugaguuuaa aaggcaccct t                                            21

<210> SEQ ID NO 23
<211> LENGTH: 21
<212> TYPE: DNA
<213> ORGANISM: Artificial sequence
<220> FEATURE:
<223> OTHER INFORMATION: inhibitor of human VEGFR-1 and VEGFR-2

<400> SEQUENCE: 23
ttgacucaaa uuuuccgugg g                                            21
```